(12) United States Patent
Saleh et al.

(10) Patent No.: US 11,573,237 B2
(45) Date of Patent: Feb. 7, 2023

(54) METHOD FOR DETECTING METHIMAZOLE

(71) Applicant: KING FAHD UNIVERSITY OF PETROLEUM AND MINERALS, Dhahran (SA)

(72) Inventors: Tawfik A. Saleh, Dhahran (SA); Mutasem M. Al-Shalafeh, Dhahran (SA); Abdulaziz A. Al-Saadi, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 17/820,908

(22) Filed: Aug. 19, 2022

(65) Prior Publication Data

US 2022/0404368 A1 Dec. 22, 2022

Related U.S. Application Data

(63) Continuation of application No. 15/920,115, filed on Mar. 13, 2018, now Pat. No. 11,474,110.

(Continued)

(51) Int. Cl.
*G01N 33/58* (2006.01)
*G01N 21/65* (2006.01)
(Continued)

(52) U.S. Cl.
CPC ......... *G01N 33/587* (2013.01); *G01N 21/658* (2013.01); *G01N 33/54373* (2013.01);
(Continued)

(58) Field of Classification Search
CPC ............... G01N 33/587; G01N 21/658; G01N 33/54373; G01N 33/94; G01N 33/49;
(Continued)

(56) References Cited

U.S. PATENT DOCUMENTS

| | | | |
|---|---|---|---|
| 2010/0285490 | A1 | 11/2010 | Dees |
| 2012/0287427 | A1 | 11/2012 | Li |
| 2015/0338348 | A1 | 11/2015 | Schultz |

FOREIGN PATENT DOCUMENTS

| | | | |
|---|---|---|---|
| CN | 102241396 B | 3/2013 | |
| CN | 102390830 B | 4/2013 | |

(Continued)

OTHER PUBLICATIONS

Tawfik A. Saleh, et al., "Graphene Dendrimer-stabilized silver nanoparticles for detection of methimazole using Surface-enhanced Raman scattering with computational assignment", Scientific Reports, vol. 6, No. 32185, Aug. 30, 2016, pp. 1-12.

(Continued)

*Primary Examiner* — Jennifer Wecker
*Assistant Examiner* — Michael Paul Shimek
(74) *Attorney, Agent, or Firm* — Oblon, McClelland, Maier & Neustadt, L.L.P.

(57) ABSTRACT

A method for analyzing or detecting methimazole ("MTZ") comprising contacting a sample suspected of containing MTZ with the dendrimer-stabilized silver nanoparticles and performing surface-enhanced Raman scattering (SERS). Graphene-dendrimer-stabilized silver nanoparticles (G-D-Ag).

11 Claims, 13 Drawing Sheets

Related U.S. Application Data

(60) Provisional application No. 62/471,524, filed on Mar. 15, 2017.

(51) Int. Cl.

| | |
|---|---|
| *G01N 33/94* | (2006.01) |
| *G01N 33/543* | (2006.01) |
| *G01N 33/493* | (2006.01) |
| *G01N 33/49* | (2006.01) |
| *B82Y 5/00* | (2011.01) |
| *B82Y 15/00* | (2011.01) |
| *C01B 32/194* | (2017.01) |
| *C08G 83/00* | (2006.01) |

(52) U.S. Cl.
CPC ............ *G01N 33/94* (2013.01); *B82Y 5/00* (2013.01); *B82Y 15/00* (2013.01); *C01B 32/194* (2017.08); *C08G 83/003* (2013.01); *G01N 33/49* (2013.01); *G01N 33/493* (2013.01)

(58) Field of Classification Search
CPC ........ G01N 33/493; B82Y 5/00; B82Y 15/00; C01B 32/194; C08G 83/003
See application file for complete search history.

(56) References Cited

FOREIGN PATENT DOCUMENTS

| CN | 102671710 B | 10/2014 |
|---|---|---|
| CN | 107503125 A | 12/2017 |
| KR | 10-1375869 B1 | 3/2014 |
| KR | 10-1582132 B1 | 1/2016 |

OTHER PUBLICATIONS

Zhimin Luo, et al., "Reduced graphene oxide/PAMAM-silver nanoparticles nanocomposite modified electrode for direct electrochemistry of glucose oxidase and glucose sensing", Biosensors and Bioelectronics, vol. 36, Issue 1, Jun.-Jul. 2012, pp. 179-185.

Wei Fan, et al., "Graphene oxide and shape-controlled silver nanoparticle hybrids for ultrasensitive single-particle surface enhanced Raman scattering (SERS) sensing", Nanoscale, vol. 6, Issue 9, 2014, pp. 4843-4851.

Tawfik A. Saleh, et al., "Ultra-trace quantitative detection of methimazole by surface-enhanced Raman spectroscopy using silver substrates", Materials Research Bulletin, vol. 91, Mar. 2017.

Rajesh, et al., "Encapsulation of silver nanoparticles into graphite grafted with hyberbranched poly(amidoamine) dendrimer and their catalytic activity towards reduction of nitro aromatics," Journal of Molecular Catalysis A: Chemical, vol. 359, pp. 88-96, Apr. 10, 2012. (Year: 2012).

Luo et al., "Reduced graphene oxide/PAMAM-silver nanoparticles nanocomposite modified electrode for direct electrochemistry of glucose oxidase and gluocose sensing," Biosensors and Bioelectronics, vol. 36, Iss. 1, pp. 179-185, Apr. 9, 2012. (Year: 2012).

Liu et al., "modified Luo, as applied to claim 1 above, further in view of Liu (Noncovalently functionalized pristine graphene/metal nanoparticle hybrid for conductive composites" Composites Science and Technology, vol. 94, pp. 1-7, Jan. 9, 2014. (Year: 2014).

Bhat et al., "Sensitive electrochemical sensing of acetaminophen and hydroquinone over single-pot synthesized stabilizer free Ag/Ag-oxide-graphene nanocomposites," Journal of Electroanalytical Chemistry, vol. 783, pp. 280-287, Nov. 2, 2016. (Year: 2016).

Shen et al., "Enzyme-Free Electrochemical Immunosensor Based on Host-Guest Nanonets Catalyzing Amplification for Procalcitonin Detection," ACS Applied Materials & Interfaces, vol. 7, pp. 4127-4134, Jan. 28, 2015. (Year: 2015).

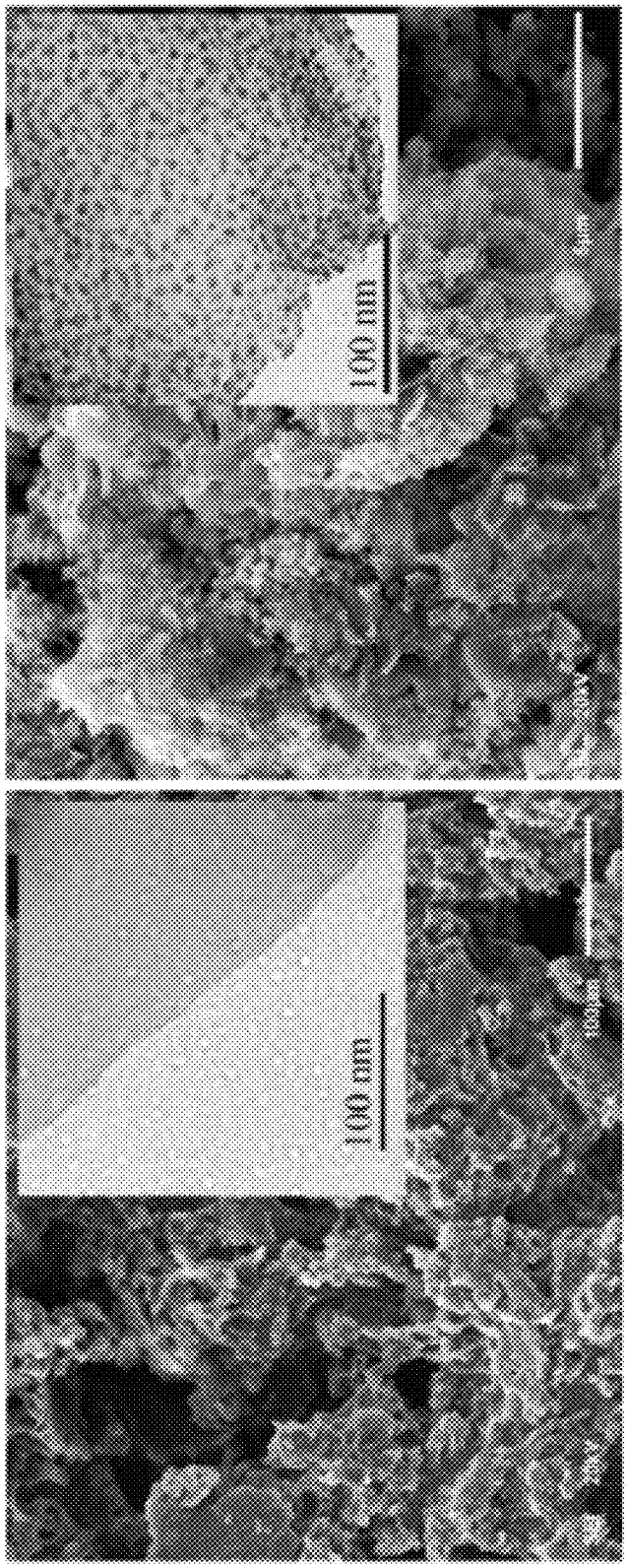
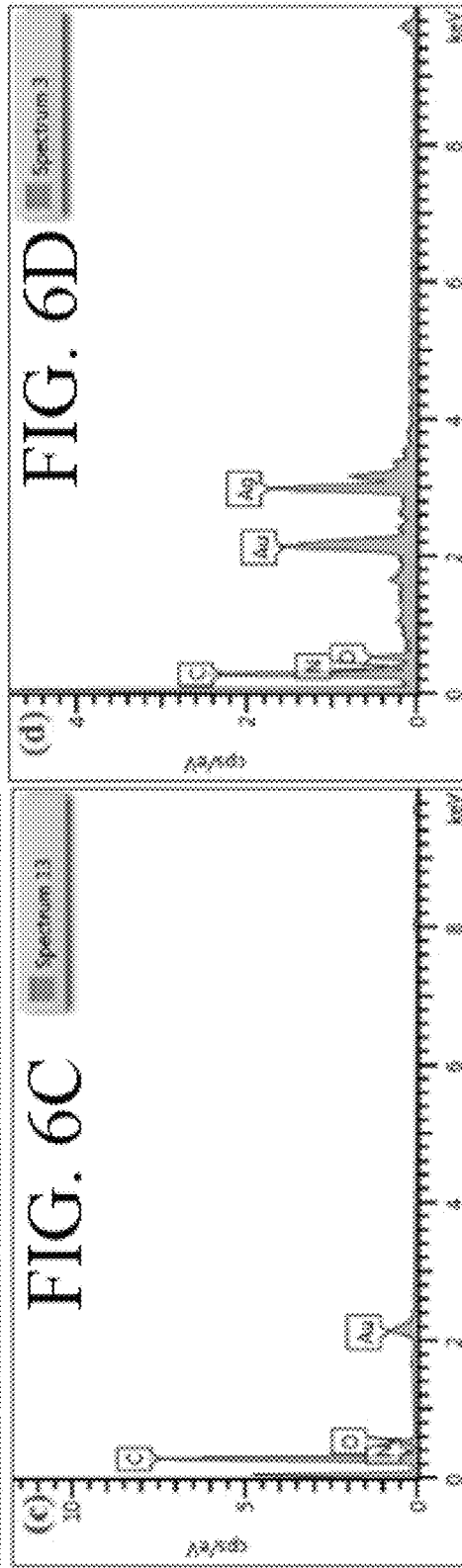
FIG. 6A  FIG. 6B  FIG. 6C  FIG. 6D

METHOD FOR DETECTING METHIMAZOLE

CROSS-REFERENCE TO RELATED APPLICATION

The present application is a Continuation of U.S. application Ser. No. 15/920,115, now allowed, having a filing date of Mar. 13, 2018 and claims benefit of priority to U.S. Provisional Application No. 62/471,524 having a filing date of Mar. 15, 2017 and which is incorporated herein by reference in its entirety.

STATEMENT REGARDING PRIOR DISCLOSURES BY THE INVENTOR OR A JOINT INVENTOR

Related technology is described by Saleh, T. A. et al. *Graphene Dendrimer-stabilized silver nanoparticles for detection of methimazole using Surface-enhanced Raman scattering with computational assignment. Sci. Rep.* 6, 32185; doi: 10.1038/srep32185 (2016) which was published Aug. 30, 2016.

BACKGROUND OF THE INVENTION

Field of the Invention. The present disclosure relates generally to graphene-dendrimer-stabilized silver nanoparticles (G-D-Ag) and polymer supported derivatives and sheets thereof.

Description of Related Art Raman spectroscopy is based on the behavior of the inelastically scattered photons upon interaction with targeted molecules, and it has been recently becoming an attractive tool for various applications. The most challenging problem with Raman techniques is the nature of the weak scattering, which hinders its effective utilization, especially for low detection limit targets. The surface-enhanced Raman scattering ("SERS") approach, however, could provide a promising strategy to solve this problem. Moreover, given the noticeable advances in instrument technology, Raman spectroscopy has begun to compete with well-established traditional analytical techniques in terms of sensitivity and ease of use; Fleischmann M., Hendra P. J. & McQuilla A. J. *Raman spectra of pyridine adsorbed at a silver electrode.* Chemical Physics Letters, 26, 2, 163-166 (1974).

In SERS, the targeted molecules are adsorbed from an aqueous solution onto nanoparticles that allow a charge transfer between analyte molecules and the particle surface, leading to an enhancement of the Raman signal. See Tian Z. Q., Ren, B. & Wu D. Y. Surface-enhanced Raman scattering: from noble to transition metals and from rough surfaces to ordered nanostructures. Journal of Physical Chemistry B, 106, 37, 9463-9483 (2002), incorporated herein by reference in its entirety. Among the various commonly used types of materials to produce enhanced scattered Raman light are high-purity film-based substrates, which include metals settled on planar surfaces such as glass, quartz, and silicon wafers; or on nanoparticle-embedded surfaces such as silica beads and polystyrene. See Vanduyne R. P., Hulteen J. C. & Treichel D. A. Atomic force microscopy and surface enhanced Raman Spectroscopy, Ag island film over polymer nanosphere surfaces supported on glass. Journal of Chemical Physics, 99, 3, 2101-2115 (1993); and Giesfeldt, K. S. et al. Studies of the optical properties of metal-pliable polymer composite materials. Applied Spectroscopy, 57, 11, 1346-1352 (2003), each incorporated herein by reference in their entirety. SERS films can also be tuned somewhat to appropriate localized surface plasmon resonances by altering various parameters such as film thickness and deposition rate, with most thicknesses of metal being between 5-60 nm. See De Jesus, M. A., Giesfeldt, K. S. & Sepaniak, M. J. Factors Affecting the Sorption of Model Environmental Pollutants onto Silver-Polydimethylsiloxane nanocomposite Raman Substrates. Applied Spectroscopy, 58, 10, 1157-1164 (2004), incorporated herein by reference in its entirety. SERS substrates of colloidal silver or gold nanoparticles can consistently yield a large signal enhancement, explained by electromagnetic and/or chemical enhancement. See Reilly T. H., Corbman J. D. & Rowlen K. L. Vapor Deposition Method for Sensitivity Studies on Engineered Surface-Enhanced Raman Scattering-Active Substrates. Analytical Chemistry, 79, 13, 5078-5081 (2007), incorporated herein by reference in its entirety.

Recently, SERS has been reported as a promising technique for quantitative and qualitative identifications of various targets. See Novikov, S. and Khriachtchev, L. Surface-Enhanced Raman Scattering of Silicon Nanocrystals in a Silica Film. Sci. Rep. 6, 27027; doi: 10.1038/srep27027 (2016), incorporated herein by reference in its entirety. It demonstrated the potential to impact the areas of analytical chemistry, biochemistry, forensics, environmental analysis, and trace analysis.

The SERS approach exhibits a number of advantages for use in low-detection limit drug analysis when compared to other analytical techniques. Due to its ultra-sensitivity, SERS was used to detect trace organic and inorganic analytes in different media. For example, some organophosphorus compounds, such as methylparathiol and dimethoate, that exist in pesticides were identified at the nanogram level. See Szymanski, H. A. Raman *Spectroscopy: Theory and Practice*. Plenum Press, Buffalo, N.Y., 1967, incorporated herein by reference in its entirety. Because water molecules scatter weakly in Raman experiments, it has made the SERS approach an attractive choice to conduct useful characterization of samples. See Creighton J. A., Blatchford C. G. & Albrecht M. G. *Plasma resonance enhancement of Raman scattering by pyridine adsorbed on silver or gold sol particles of size comparable to the excitation wavelength*, Journal of the Chemical Society, Faraday Transactions, 75, 790-798 (1979); Powell, J. A. et al. *Programmable SERS active substrates for chemical and biosensing applications using amorphous/crystalline hybrid silicon nanomaterial.* Sci. Rep. 6, 19663; doi: 10.1038/srep19663 (2016); and Doğan, I. et al. Analysis of temporal evolution of quantum dot surface chemistry by *surface-enhanced Raman scattering*. Sci. Rep. 6, 29508; doi: 10.1038/srep29508 (2016), each incorporated herein by reference in their entirety.

However, one of the most challenging tasks in developing an effective analytical SERS based method is the fabrication of the right metal colloid substrate, such as silver, that can exhibit a hotspot within the nanoparticles and subsequently achieve extremely high enhancement. See Aroca, R. F., Alvarez-Puebla, R. A., Pieczonka, N., Sanchez-Cortez, S. and Garcia-Ramos, J. V. *Surface-enhanced Raman scattering on colloidal nanostructures. Advances in Colloid and Interface Science,* 116, 1-3 45-61 (2005), each incorporated herein by reference in its entirety. Since it is required to have more nanoparticles to hook the targeted molecules, the use of a support to load the silver nanoparticles may control the agglomeration that diminishes the enhancement in SERS. Dendrimers, which represent a new class of polymeric nanoscale compounds, are promising candidates for SERS applications due to their homogeneous nature and unique tree-like structure. They have been found to be useful in the health industry, and in pharmaceutical and materials applications. See Abbasi, E. et al. *Dendrimers: synthesis, applications, and properties*. Nanoscale Research Letters 9, 247-257 (2014), incorporated herein by reference in its entirety. In addition, dendrimers are considered as one of the most appropriate encapsulating agents for the stabilization of metal nanoparticles (NPs), due to their large size and the presence of a unique three-dimensional architecture of the dendrons that prevents leaching of the NPs during the course of the reaction. See Jiang Y., Gao Q. *Heterogeneous Hydrogenation Catalyses over Recyclable Pd(0) Nanoparticle Catalysts Stabilized by PAMAM-SBA-15 Organic-Inorganic Hybrid Composites*. J. Am. Chem. Soc. 128, 716-717 (2006), incorporated herein by reference in its entirety. The polyamidoamine dendrimers are considered the favored choice for pharmaceutical applications, due to their regular structure, large size, and chemical versatility. See Rajesh R., Kumar S. S., & Venkatesan R. *Efficient degradation of azo dyes using Ag and Au nanoparticles stabilized on graphene oxide functionalized with PAMAM dendrimers*. New J. Chem. 8, 1551-1558 (2014), incorporated herein by reference in its entirety.

Several analytical procedures have been reported for the determination of a methimazole-based drug (also known as 1-methyl-2-mercaptoimidazole and tapazole), which is considered as an antihormone drug widely used to treat hyperthyroidism. These methods include molecularly imprinted biomimetic sensing, fluorescence, thin layer chromatography, coulometry, conductometry, and high-performance liquid chromatography with ultraviolet detection. See Pan, M. et al. *Molecularly imprinted biomimetic QCM sensor involving a poly(amidoamine) dendrimer as a functional monomer for the highly selective and sensitive determination of methimazole, Sensors and Actuators B*: Chemical, 207, 588-595 (2015); Farzampour L., Amjadi M., *Sensitive turn-on fluorescence assay of methimazole based on the fluorescence resonance energy transfer between acridine orange and silver nanoparticles*, Journal of Luminescence, 155, 226-230 (2014); Aletrari M., Kanari P., Partassides D., Loizou E., *Study of the British Pharmacopeia method on methimazole (thiamazole) content in carbimazole tablets*, Journal of Pharmaceutical and Biomedical Analysis, 16, 785-792 (1998); Nikolic K., Velasevic K. *Coulometric determination of methimazole*, Pharmazie, 42, 698-700 (1987); Berka A., Velasevic K., Nikolic K. *Conductometric determination of methimazole*, Pharmazie, 44, 499-500 (1989); and Moretti, G. et al. *Determination of thyreostatic residues in cattle plasma by high-performance liquid chromatography with ultraviolet detection*, Journal of Chromatography: Biomedical Applications, 616, 291-296 (1993), each incorporated herein by reference in their entirety. No SERS attempts with the use of graphene dendrimeric-based substrates have been reported to detect low-concentration samples of methimazole ("MTZ").

Other work in this field includes that of Liao X. et al. *Au—Ag—Au double shell nanoparticles-based localized surface plasmon resonance and surface-enhanced Raman scattering biosensor for sensitive detection of 2-mercapto-1-methylimidazole*. Talanta. 117, 203-208 (2013); Ma P. et al. *Highly sensitive SERS probe for mercury(II) using cyclodextrin-protected silver nanoparticles functionalized with methimazole*. Microchimica Acta. 181, 975-98 (2014); Economou A., Tzanavaras P. D., Notou M. & Themelis D. G. *Determination of methimazole and carbimazole by flow-injection with chemiluminescence detection based on the inhibition of the Cu(II)-catalysed luminol-hydrogen peroxide reaction*. Analytica Chimica Acta. 505, 129-133 (2004); Sun J. et al. Electrochemical Detection of *Methimazole by Capillary Electrophoresis at a Carbon Fiber Microdisk Electrode*. Electroanalysis. 17, 1675-1680 (2005); Yazhen W. *Electrochemical determination of methimazole based on the acetylene black/chitosan film electrode and its application to rat serum samples*. Bioelectrochemistry. 81, 86-90 (2011); Zakrzewski R. *Determination of Methimazole in Pharmaceutical Preparations using an HPLC Method Coupled with an Iodine Azide Post-Column Reaction*. Journal of Liquid Chromatography & Related Technologies. 32, 383-398 (2009); and Molero L., Faundez M., Valle M. A., del Rio R. & Armijo F. *Electrochemistry of methimazole on fluorine-doped tin oxide electrodes and its square-wave voltammetric determination in pharmaceutical formulations*. Electrochimica Acta. 88, 871-876 (2013).

In this work the inventors used graphene as a support, modified with a dendrimer, to allow controlled silver nanoparticles to be linked to its branches. The prepared graphene linked with dendrimer-stabilized silver nanoparticles (G-D-Ag) was used as a SERS substrate for MTZ detection.

BRIEF SUMMARY OF THE INVENTION

A method for analyzing or detecting methimazole ("MTZ") comprising contacting a sample suspected of containing MTZ with the dendrimer-stabilized silver nanoparticles and performing surface-enhanced Raman scattering (SERS). Graphene-dendrimer-stabilized silver nanoparticles (G-D-Ag) such as those comprising a graphene oxide sheet supported polyamidoamine ("PAMAM") dendrimer represented by formula (I):

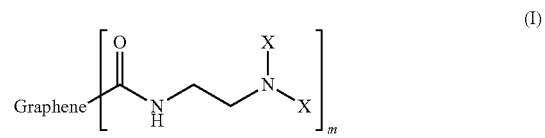

wherein X is -A-B—$NH_2$, -A-B—N-(A-B—$NH_2$)$_2$, or -A-B—N—[A-B—N-(A-B—$NH_2$)$_2$]$_2$;

A is —$CH_2CH_2C(O)$—;

B is —$NHCH_2CH_2$—;

Graphene represents the graphene oxide sheet; and m is a positive integer in the range of 2-100; and wherein a weight ratio of the silver nanoparticles relative to the graphene oxide sheet is in the range of 1:1 to 3:1.

Other advantages and features will become more clearly apparent from the following description of particular embodiments of the invention, which are given by way of non-limiting example and illustrated in the figures listed below.

BRIEF DESCRIPTION OF THE DRAWINGS

FIG. 6A. Typical SEM image of G-D.

FIG. 6B. Typical SEM image of G-D-Ag.
FIG. 6C. EDX spectra of G-D.
FIG. 6D. EDX spectra of G-D-Ag.

DETAILED DESCRIPTION OF THE INVENTION

Figure 1:
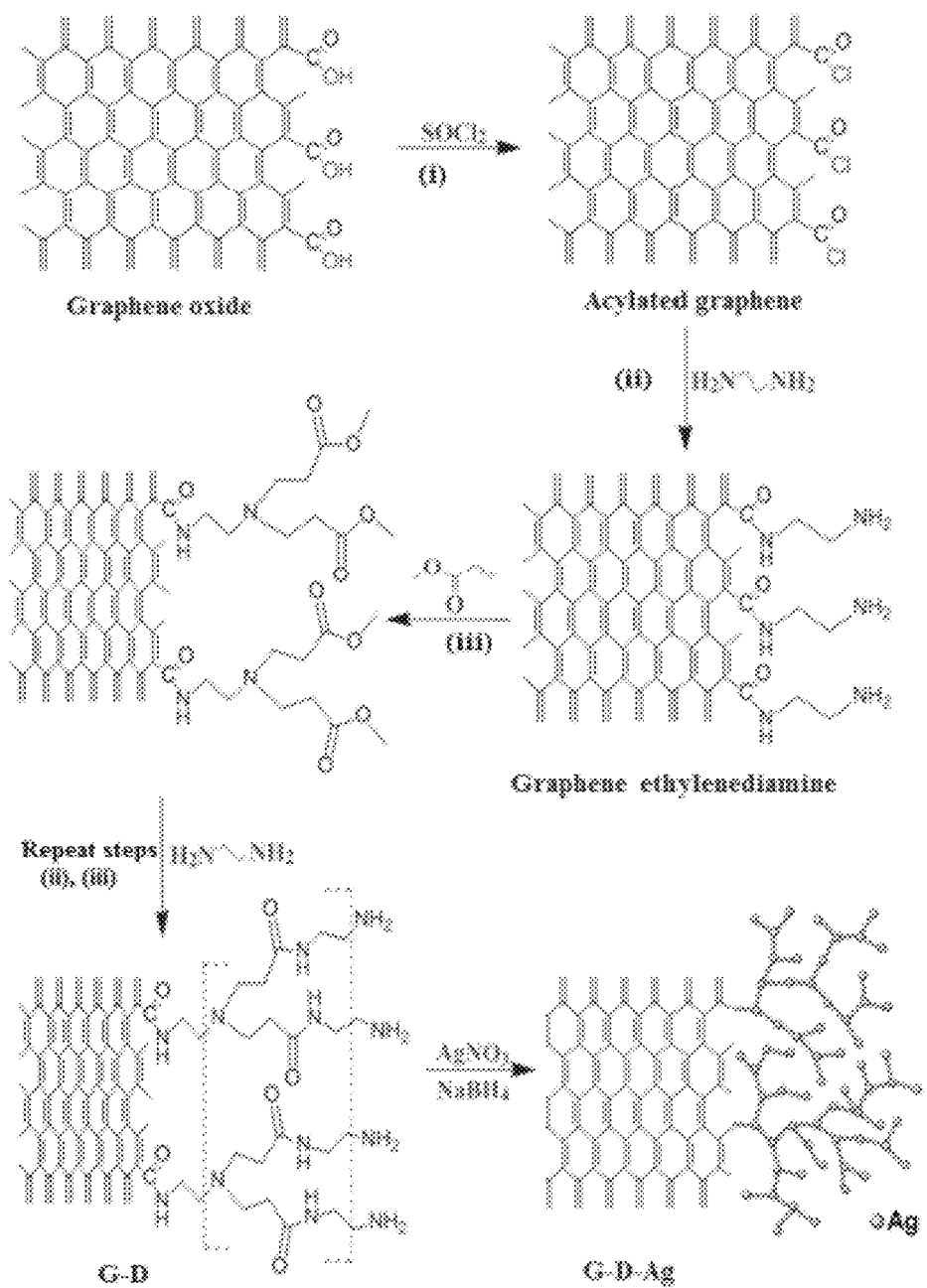
FIG. 1: Illustration explaining the synthesis steps of the graphene-polyamidoamine dendrimer-silver G-D-Ag.

Hyperthyroidism (overactive thyroid) is a condition in which your thyroid gland produces too much of the hormone thyroxine. Hyperthyroidism can accelerate your body's metabolism significantly, causing sudden weight loss, a rapid or irregular heartbeat, sweating, and nervousness or irritability. Several treatment options are available for hyperthyroidism. Anti-thyroid medications and radioactive iodine are used to slow the production of thyroid hormones. Sometimes, treatment of hyperthyroidism involves surgery to remove all or part of the thyroid gland. Although hyperthyroidism can be serious if it is ignored most people respond well once hyperthyroidism is diagnosed and treated. Hyperthyroidism is also found in animals. Clinical hyperthyroidism in cats and dogs is produced from excessive secretion of the thyroid hormones, $T_4$ and $T_3$, resulting in signs that reflect an increased metabolic rate. It is most common in middle-aged to old cats and is less frequently seen in dogs.

Methimazole (1-methylimidazole-2-thiol) is a white, crystalline substance that is freely soluble in water. It differs chemically from the drugs of the thiouracil series primarily because it has a 5- instead of a 6-membered ring. In some embodiments a methimazole derivative or prodrug may be detected, such as those described by U.S. Pat. No. 6,365,616 B1 or by Roy, et al., *J. Am. Chem. Soc.*, 2005, 127 (43), pp 15207-15217 (both incorporated by reference).

Methimazole is readily absorbed in the gastrointestinal tract, metabolized in the liver, and excreted in the urine. Methimazole prevents the thyroid gland from producing too much thyroid hormone. It is used to treat hyperthyroidism but can cause side-effects such as agranulocytosis and liver inflammation.

Methimazole is contraindicated in the presence of hypersensitivity to the drug or any of the other product components. Methimazole readily crosses placental membranes and can cause fetal harm, particularly when administered in the first trimester of pregnancy and if methimazole is used, the lowest possible dose to control the maternal disease should be given.

Agranulocytosis is a potentially a life-threatening adverse reaction of Methimazole therapy. The drug should be discontinued in the presence of agranulocytosis, aplastic anemia (pancytopenia), ANCA-positive vasculitis, hepatitis, or exfoliative dermatitis, and the patient's bone marrow indices should be monitored. Although there have been reports of hepatotoxicity (including acute liver failure) associated with Methimazole, the risk of hepatotoxicity appears to be less with Methimazole than with propylthiouracil, especially in the pediatric population. Symptoms suggestive of hepatic dysfunction (anorexia, pruritus, right upper quadrant pain, etc.) should prompt evaluation of liver function (bilirubin, alkaline phosphatase) and hepatocellular integrity (ALT, AST). Drug treatment should be discontinued promptly in the event of clinically significant evidence of liver abnormality including hepatic transaminase values exceeding 3 times the upper limit of normal. Methimazole can cause hypothyroidism necessitating routine monitoring of TSH and free T4 levels with adjustments in dosing to maintain a euthyroid state. Because the drug readily crosses placental membranes, Methimazole can cause fetal goiter and cretinism when administered to a pregnant woman. For this reason, it is important that a sufficient, but not excessive, dose be given during pregnancy.

LFTs (liver function tests) are a group of blood tests that can help to show how well a person's liver is working. LFTs include measurements of albumin, various liver enzymes (ALT, AST, GGT and ALP), bilirubin, prothrombin time, cholesterol and total protein.

Graphene is an allotrope of carbon in the form of a two-dimensional, atomic-scale, honey-comb lattice in which one atom forms each vertex. It is the basic structural element of other allotropes, including graphite, charcoal, carbon nanotubes and fullerenes. Graphenes include bulk graphite having more than ten graphene layers stacked, few-layer graphene (FLG): Two-dimensional material consisting of three to ten well defined stacked graphene layers, bilayer graphene (2LG) two-dimensional material consisting of two well-defined stacked graphene layers; and monolayer graphene (1LG) a single layer of carbon atoms with each atom bound to three neighbors in a honeycomb structure. Carbon nanotubes, which have different structures and properties than most graphenes, may be excluded.

Figure 2:
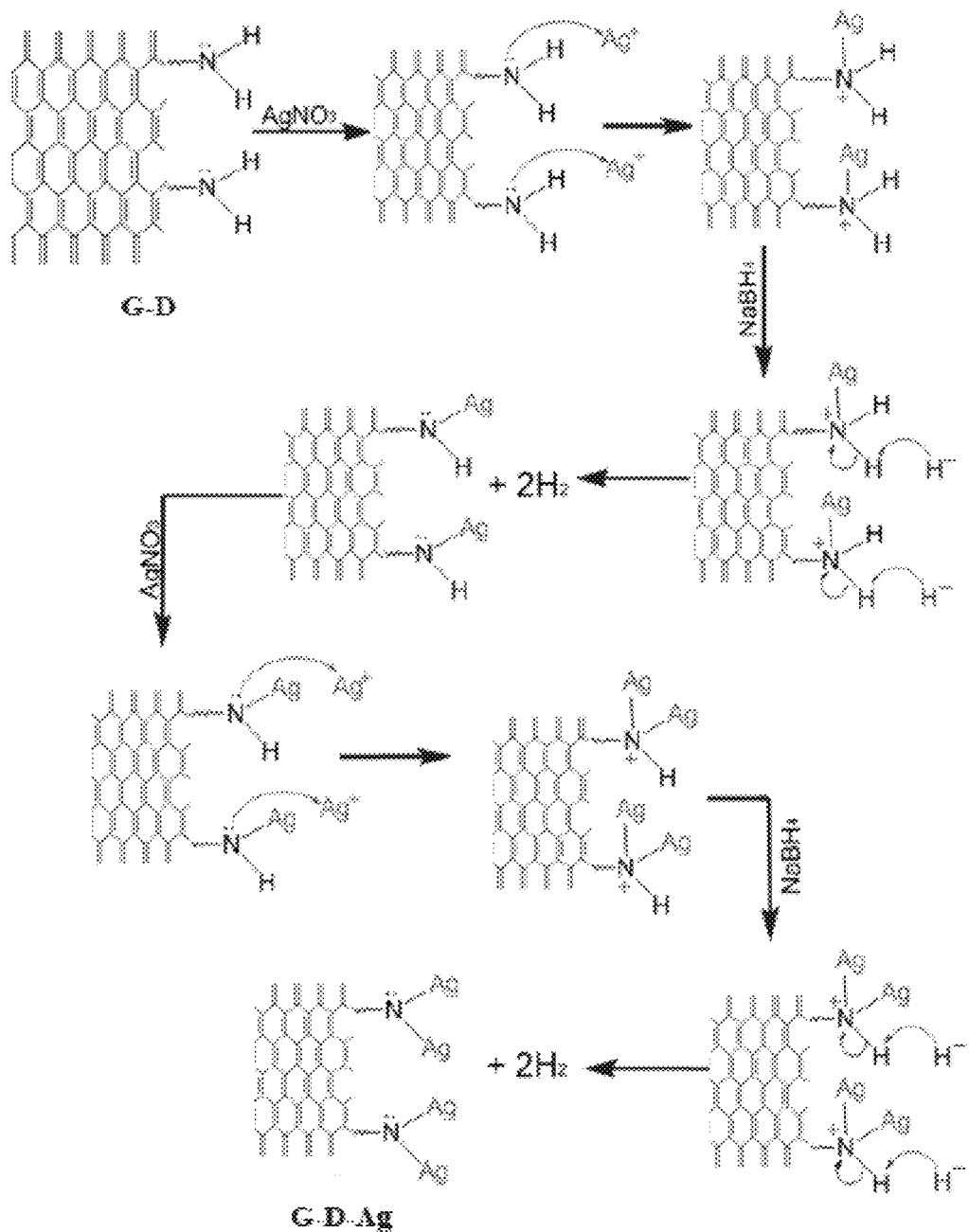
FIG. 2: Mechanism of the stabilization of the AgNPs on the graphene through the dendrimer for the preparation of graphene-polyamidoamine dendrimer-silver (G-D-Ag).

Graphene oxides are depicted in FIGS. 1 and 2. Acylated graphenes contain an acyl halide group, such as a —COX functional group, as depicted by FIG. 1, second diagram, which consists of a carbonyl group singly bonded to a halogen atom X. Halide anions include fluoride ($F^-$), chloride ($Cl^-$), bromide ($Br^-$), iodide ($I^-$) and astatide ($At^-$) with acyl chlorides and acyl iodides being preferred. A graphene functionalized with a dendrimer may be produced by reacting an acylated graphene (e.g., graphene containing acyl halides) with ethylenediamine or another diamine.

Dendrimers are repetitively branched molecules. Synonymous terms for dendrimer include arborols and cascade molecules. A dendrimer is typically symmetric around a core and often adopts a spherical three-dimensional morphology. In the invention dendrimers are attached to a graphene, such as a graphene oxide surface. Dendrimers are classified by generation, which refers to the number of repeated branching cycles that are performed during its synthesis. For example, if a dendrimer is made by convergent synthesis and the branching reactions are performed onto the core molecule three times, the resulting dendrimer is considered a third generation dendrimer. Each successive generation results in a dendrimer roughly twice the molecular weight of the previous generation. Higher generation dendrimers, such as generations 4, 5, 6, 7, 8, 9, 10, 11 or 12 have more exposed functional groups on the surface which can later be used to customize the dendrimer for a given application. These include polyamidoamine dendrimer which is described in the Example.

Polyamidoamine (PAMAM) dendrimers are hyperbranched polymers with unparalleled molecular uniformity, narrow molecular weight distribution, defined size and shape characteristics and a multifunctional terminal surface. These nanoscale polymers consist of an ethylenediamine core, a repetitive branching amidoamine internal structure and a primary amine terminal surface.

In some embodiments, the ethylene diamine moiety may be replaced by another diamine that can be used to form a dendrimer, including diamines having 3-7 carbon atoms. These include 3 carbon diamines like 1,2-diaminopropane or 1,3-diaminopropane, 4 carbon diamines such as putrescine (butane-1,4-diamine), 5 carbon diamines such as cadaverine (pentane-1,5-diamine) and 6 carbon diamines such as hexamethylenediamine (hexane-1,6-diamine).

Methyl acrylate is used in the Example to produce dendrimers. In other embodiments, other acrylates may be used including acrylates containing 5-21 carbon chain lengths and others described by Sabahi, et al., Volume: 29 issue: 7, page(s): 941-953 (2014, incorporated by reference).

Dendrimers are "grown" off a central core in an iterative manufacturing process, with each subsequent step representing a new "generation" of dendrimer. Increasing generations (molecular weight) produce larger molecular diameters, twice the number of reactive surface sites and approximately double the molecular weight of the preceding generation. PAMAM dendrimers also assume a spheroidal, globular shape at Generation 4 and. Their functionality is readily tailored, and their uniformity, size and highly reactive "molecular Velcro" surfaces are the functional keys to their use. Dendrimers such as PAMAM dendrimers appearing in the Example below are described and incorporated by references to the references cited herein.

Silver particles include the silver nanoparticles described in the Example and Figures. Dendrimer templated construction of silver nanoparticles is described by Castonguay, et al., *Advances in Colloid and Interface Science*, Volume 160, Issues 1-2, 15 Oct. 2010, Pages 76-87; and encapsulation of silver nanoparticles into graphite grafted with hyperbranched poly(amidoamine) dendrimer and their catalytic activity towards reduction of nitro aromatics by Rajesh, et al., Journal of Molecular Catalysis A: Chemical, Volume 359, July 2012, Pages 88-96, both of which are incorporated by reference. The use of silver particles hooked the graphene surface support via dendrimers avoided problems associated with the use of naked silver particles such as agglomeration.

Those skilled in the art will select silver compounds and reducing agents suitable for decorating a dendrimer with silver nanoparticles as shown by FIG. 2. In general, different reducing agents such as sodium citrate, ascorbate, sodium borohydride ($NaBH_4$), elemental hydrogen, polyol process, Tollens reagent, N, N-dimethylformamide (DMF), and poly (ethylene glycol)-block copolymers are used for reduction of silver ions ($Ag^+$) in aqueous or non-aqueous solutions. In the Example, sodium borohydride is used as a reducing agent to decorate or bind silver nanoparticles to a dendrimer. Formation of silver nanoparticles by reduction is also described by and incorporated by reference to Iravani, et al., *Synthesis of silver nanoparticles: chemical, physical and biological methods*, Res Pharm Sci. 2014 November-December; 9(6): 385-406.

In some embodiments only silver particles will be associated with or decorated on the dendrimer component of the invention and metals such as Au, Cu, Fe, Ir, Ni, Os, Pd, Pt, and Ru and alloys (or metal compounds such as metal sulfides) thereof will not be present.

Nanoparticles or nanosized particles refer to particles having a mean particle size ranging from 1 nm to ≤100 nm which range includes all intermediate values and subranges, such as 1, 2, 5, 10, 15, 20, 25, 30, 35, 40, 45, 50, 60, 70, 75, <100 and 100 nm, for example, as determined using transmission electron microscopy ("TEM"). In some preferred embodiments silver nanoparticles will have mean diameters of less than 35, 36, 37, 38, 39 or 40 nm. Nanoparticles according to the invention advantageously may have a mean diameter of less than 1, 2, 5, 10, 15, 20, 25 or 50 nm and encompass particles that are 1, 2, 3, 4, 5, 10, 15, 20, 25, 30, 40, 50, 60, 70, 80, 90, 100% or more smaller or larger than those described in the Example and Figures (or any intermediate value or subrange of the ranges above).

Pharmaceutical products. Among its other uses, the method of the invention can be applied to detect methimazole in a pharmaceutical composition. The invention may be used to assess product purity, detect counterfeit drugs, detect batch-to-batch differences in methimazole preparations, detect or monitor degradation of methimazole over time or of methimazole stored under different temperatures or conditions, or detect spatial or lateral distribution of methimazole in a tablet, granule or other pharmaceutical preparation, assess particle size of a particulate pharmaceutical preparation, or to help explain inconsistencies in dissolution profiles of methimazole.

Biological samples include samples from both in vivo and in vitro sources, such as samples taken from a patient taking methimazole or from cells exposed to methimazole. Biological samples include blood, plasma, serum, and urine or other samples suspected of containing methimazole.

Environmental, Industrial, Commercial or other samples. The method described herein may detect methimazole in virtually any form, including in forensic samples, environmental samples, or industrial samples.

Detection sensitivity. In some embodiments, the detection limit of a method of the invention will be at least $10^{-9}$, $10^{-10}$, $10^{-11}$, or $10^{-12}$ M (or any intermediate value within this range). As shown in the Example below, a low detection limit of $1.43 \times 10^{-12}$ M was successfully obtained.

Selected embodiments of the invention include, but are not limited to those described below.

Embodiment 1. A Graphene-dendrimer-stabilized silver nanoparticles (G-D-Ag) that comprises a graphene oxide sheet supported polyamidoamine ("PAMAM") dendrimer represented by formula (I):

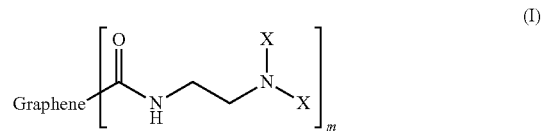

wherein X is -A-B—$NH_2$, -A-B—N-(A-B—$NH_2$)$_2$, or -A-B—N—[A-B—N-(A-B—$NH_2$)$_2$]$_2$, A is —$CH_2CH_2C(O)$—;

B is —$NHCH_2CH_2$—;

Graphene represents the graphene oxide sheet;

wherein m is a positive integer in the range of 2-100 (or any intermediate integer value or subrange such as 2, 3, 4, 5, 6, 7, 8, 9, 10, 20, 30, 40, 50, 60, 70, 80, 90, 95, 99, or 100); and silver nanoparticles bound to the graphene oxide sheet supported polyamidoamine ("PAMAM") dendrimer;

wherein a weight ratio of the silver nanoparticles relative to the graphene oxide sheet is in the range of 1:1 to 3:1 (or any intermediate value or subrange such as 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9 or 1:3.

Embodiment 2. The G-D-Ag of embodiment 1, wherein the silver nanoparticles have a mean diameter of no more than 40 nm, such as 1, 2, 3, 4, 5, 6, 7, 8, 9, 10, 11, 12, 13, 14, 15, 16, 17, 18, 19, 20, 22, 25, 30, 32, 35, 36, 37, 38, 39, <40 or 40 nm (or any intermediate value or subrange).

Embodiment 3. The G-D-Ag of embodiment 1, wherein the silver nanoparticles have a mean diameter of no more than 20 nm.

Embodiment 4. A SERS-active material comprising the G-D-Ag of embodiment 1 and a Surface-Enhanced Raman Scattering (SERS) active substrate that comprises silica glass coated with at least one layer of the G-D-Ag.

Embodiment 5. A SERS-active material comprising the G-D-Ag of embodiment 1 and a Surface-Enhanced Raman Scattering (SERS) active substrate that comprises silica glass coated with at least one layer of the G-D-Ag, wherein said at least one layer of G-D-Ag in aggregate ranges in thickness from 10 nm to 100 μm, such as 10, 20, 30, 40, 50, 60, 70, 80, 90, 100, 200, 300, 400, 500, 600, 700, 800, 900, or <1,000 nm, or such as 1, 10, 20, 30, 40, 50, 60, 70, 80, 90, <100, or 100 μm (or any intermediate value or subrange).

Embodiment 6. A method for detecting methimazole ("MTZ") or determining a concentration of methimazole in a sample comprising contacting the sample containing or suspected of containing MTZ with the dendrimer-stabilized silver nanoparticles of embodiment 1 and performing surface-enhanced Raman scattering (SERS).

Embodiment 7. The method of embodiment 6 for determining a concentration of methimazole in at least one sample, comprising:

mixing the at least one sample with G-D-Ag at a volume ratio of 1:1 to 8:1 to prepare at least one analyte; and performing surface-enhanced Raman scattering ("SERS") by acquiring a SERS spectrum of the at least one analyte by Raman spectroscopy;

determining the concentration of methimazole in the at least one sample by comparing the peak intensity of a Raman band of methimazole obtained from the SERS spectrum of the at least one analyte to a standard linear regression curve that plots known concentrations of methimazole against peak intensities of the Raman band.

Embodiment 8. The method of embodiment 6, wherein the sample is a pharmaceutical, drug or chemical sample and not a biological sample from a subject.

Embodiment 9. The method of embodiment 6, further comprising determining purity of a nonbiological pharmaceutical sample of methimazole, whether the sample is counterfeit, whether there is a difference between two or more methimazole samples, whether a methimazole sample has degraded, spatial or lateral distribution of methimazole in a sample that is a tablet or granule, or determining a particle size of a pharmaceutical preparation containing methimazole. Peak intensities from different samples may be compared to those of control samples of known purity, those of methimazole stored for a particular period of time or under particular temperature, humidity or other physical or chemical conditions, or to those of samples having particular particle sizes or spatial distributions of methimazole.

Embodiment 10. The method of embodiment 6, wherein the sample is serum, plasma, urine or other biological sample.

Embodiment 11. The method of embodiment 6, wherein the sample is human serum, plasma, urine or other human biological sample.

Embodiment 12. The method of embodiment 6, wherein the sample is serum, plasma, urine or other biological sample obtained from Felts *catus* (domestic cat) or other member of the family Felidae.

Embodiment 13. The method of embodiment 6, wherein the sample is from a subject having hyperthyroidism or at risk thereof.

Embodiment 14. The method of embodiment 6, wherein the sample is from a female who is pregnant or who may become pregnant.

Embodiment 15. The method of embodiment 6, wherein the sample is from a subject having, genetically predisposed to having, or at risk of having agranulocytosis, aplastic anemia (pancytopenia), ANCA-positive vasculitis, exfoliative dermatitis, hepatitis, or hepatatic dysfunction or at least one symptom thereof; or wherein the sample is from a subject having anorexia, pruritus, or right upper quadrant pain or other symptom of hepatic dysfunction or wherein the sample is from a subject having an abnormal liver function test.

Embodiment 16. The method of embodiment 6, further comprising detecting at least one other analyte besides methimazole.

Embodiment 17. A method of synthesizing the G-D-Ag of embodiment 1, comprising: reacting an acylated graphene with ethylenediamine to form a dendrimer G0; successively reacting the dendrimer G0 with methyl acrylate followed by ethylenendiamine once to form a graphene sheet supported PAMAM dendrimer G1, wherein X is -A-B—$NH_2$, twice to form a graphene sheet supported PAMAM dendrimer G2, wherein X is -A-B—N-(A-B—$NH_2$)$_2$, or three times to form a graphene sheet supported PAMAM dendrimer G3, wherein X is -A-B—N-[A-B—N-(A-B—$NH_2$)$_2$]$_2$; and reacting the graphene sheet supported PAMAM dendrimer G1, G2, or G3 with a silver(I) salt in the presence of a reducing agent to form the G-D-Ag.

Embodiment 18. A system for analyzing a pharmaceutical preparation of methimazole or a biological sample containing methimazole comprising the dendrimer-stabilized silver nanoparticles (G-D-Ag), Raman spectroscope (e.g., excitation source, sampling apparatus, and detector), communications elements, data processing elements, software or computer equipment for analyzing, processing and storing these data, displays or other data output elements, and/or instructions for use in analyzing MTZ.

Embodiment 19. A kit for detecting methimazole in a pharmaceutical or biological sample comprising the dendrimer-stabilized silver nanoparticles (G-D-Ag), and optionally one or more reagents suitable for detecting MTZ in conjunction with G-D-Ag, one or more positive control samples, one or more negative control samples, one or more containers or reaction vessels, packaging materials and/or instructions for use in detecting MTZ, or promotional materials.

A sample holder comprising the Graphene-dendrimer-stabilized silver nanoparticles (G-D-Ag) of claim 1 and (a) a cuvette with dimensions of 0.5 to 2.0 cm in diameter and 0.3 to 2.0 cm in length containing or coated with the G-D-Ag, or (b) a silica glass slide having with dimensions of 3 to 10 cm in length and 1 to 5 cm in width that is coated on at least one side with the G-D-Ag. Thickness of a coating or layer of G-D-Ag may range from 1, 2, 5, 10, 20, 50, 100, 500, 1,000 nm to >1, 2, 5, 10, 20, 50, 100 or >100 µM or any intermediate value or subrange.

EXAMPLE

As shown herein graphene functionalized with polyamidoamine dendrimer, decorated with silver nanoparticles (G-D-Ag), was synthesized and evaluated as a substrate with surface enhanced Raman scattering (SERS) for methimazole (MTZ) detection. Sodium borohydride was used as a reducing agent to cultivate silver nanoparticles on the dendrimer. The obtained G-D-Ag was characterized by using UV-vis spectroscopy, scanning electron microscope (SEM), high-resolution transmission electron microscope (TEM), Fourier-transformed infrared (FT-IR) and Raman spectroscopy. The SEM image indicated the successful formation of the G-D-Ag. The behavior of MTZ on the G-D-Ag as a reliable and robust substrate was investigated by SERS, which indicated mostly a chemical interaction between G-D-Ag and MTZ. The bands of the MTZ normal spectra at 1538, 1463, 1342, 1278, 1156, 1092, 1016, 600, 525 and 410 cm$^{-1}$ were enhanced due to the SERS effect. Correlations between the logarithmical scale of MTZ concentrations and SERS signal intensities were established and a low detection limit of $1.43 \times 10^{-12}$ M was successfully obtained. The density functional theory (DFT) approach was utilized to provide reliable assignment of the key Raman bands.

Experimental Procedure

Chemicals and Materials. Methimazole (MTZ) "1-Methyl-2-imidazolethiol "(analytical standard, ≥99% purity), CAS number 60560, was purchased from Sigma-Aldrich. Silver nitrate (AgNO$_3$, 99.8%), product number 30087, was purchased from BDH-Chemicals Ltd Poole England. Sodium borohydride (NaBH$_4$), product number 63390, was purchased from Allied Signal. Ethylenediamine (≥99.5%), product number 03550, methyl acrylate (99%), CAS number 76778, thionyl chloride (SOCl$_2$, ≥99%), product number 230464, and potassium bromide (KBr, ≥99%), product number 221864, were purchased from Sigma-Aldrich. Solutions were prepared with ultrapure water obtained from a water purification system (Ultra Clear™ Lab Water Systems, Siemens Water Technologies USA).

Synthesis of graphene dendrimer silver composite. FIG. 1 shows the preparation steps of dendrimer functionalization with silver. About 0.2 g of the prepared graphene nanosheets was dispersed in 20 ml of SOCl$_2$ by sonication in an ultrasound bath for 30 min and stirred for 12 h at 60° C.; the mixture was then filtered. The obtained material was dried overnight at room temperature. Next, 10 ml of ethylenediamine was added to the solid product, the reaction mixture was sonicated for 3 h at 60° C. and stirred for another 12 h at room temperature. The solid product was collected by centrifugation at 10,000 rpm/min for 10 min and dried overnight at room temperature.

The last solid product was suspended in 10 ml methanol and was added dropwise to 25 ml of 1:4 methyl acrylate—methanol solution under stirring. The reaction mixture was treated in an ultrasonic bath at 60° C. for 2 hours and stirred for another 12 h at room temperature.

The solid product was collected by centrifugation at 10,000 rpm/min for 10 min and dried overnight at room temperature. Afterward, the obtained material was immersed in 10 ml methanol, and then a 1:1 mixture of 10 ml of ethylenediamine—methanol was added at a rate 1 drop/sec to the solution. The solution was placed in an ultrasonic bath at 50° C. for 5 h and stirred for another 10 h at room temperature. The solid product was collected by centrifugation and dried overnight at room temperature. The steps were repeated for methyl acrylate and ethylenediamine until reaching the third-generation. The third-generation polyamidoamine dendrimer on the graphene (G-D) presented a typical morphology when compared to the others obtained using higher dendrimer concentrations.

The solid of this material was dispersed in 20 ml deionized water by sonication in an ultrasound bath for 10 min. Then, 10 ml of 0.2 M AgNO$_3$ was added dropwise with the previously dispersed solid and the mixture was stirred for 1 hour. Then, 10 ml of a freshly prepared solution of NaBH$_4$ was added to the solution and the solution was kept under stirring for another 5 h. Finally, the mixture was filtered, and the obtained material was washed with deionized water several times. The greenish yellow isolated solid was dried overnight at room temperature. The stabilization mechanism of the silver nanoparticles (AgNPs) on the graphene nanosheets through the dendrimers is shown in FIG. 2. The abbreviation used for graphene modified with a third-generation polyamidoamine dendrimer is G-D, while for graphene-dendrimer-silver nanoparticles it is G-G-Ag.

Material Characterization. Scanning Electron Microscope, JSM-6610LV, JEOL at 20 kV acceleration voltage equipped with energy-dispersive X-ray spectroscope, Mapping and transmission electron microscope (TEM, FEI Tecnai TF20) were employed to investigate the morphological and microstructural attributes of the synthesized material. The UV-Visible spectra of the graphene and G-D-Ag were recorded on a genesis 10S UV-Vis spectrophotometer (Thermo Scientific), using standard quartz cuvette at room temperature between 250-650 nm. The samples were prepared by dilution the stock solution 4× with distilled water. FT-IR spectra of samples were recorded using a Perkin-Elmer IR spectrophotometer using potassium bromide (KBr) pellets, the pellet was designed by blending the sample and KBr with a ratio of 1:100. The FT-IR measurement was scanned at a range from 400 to 4000 cm$^{-1}$. The He—Ne laser source operating at 0.5 W was utilized for sample excitation.

Figure 10:
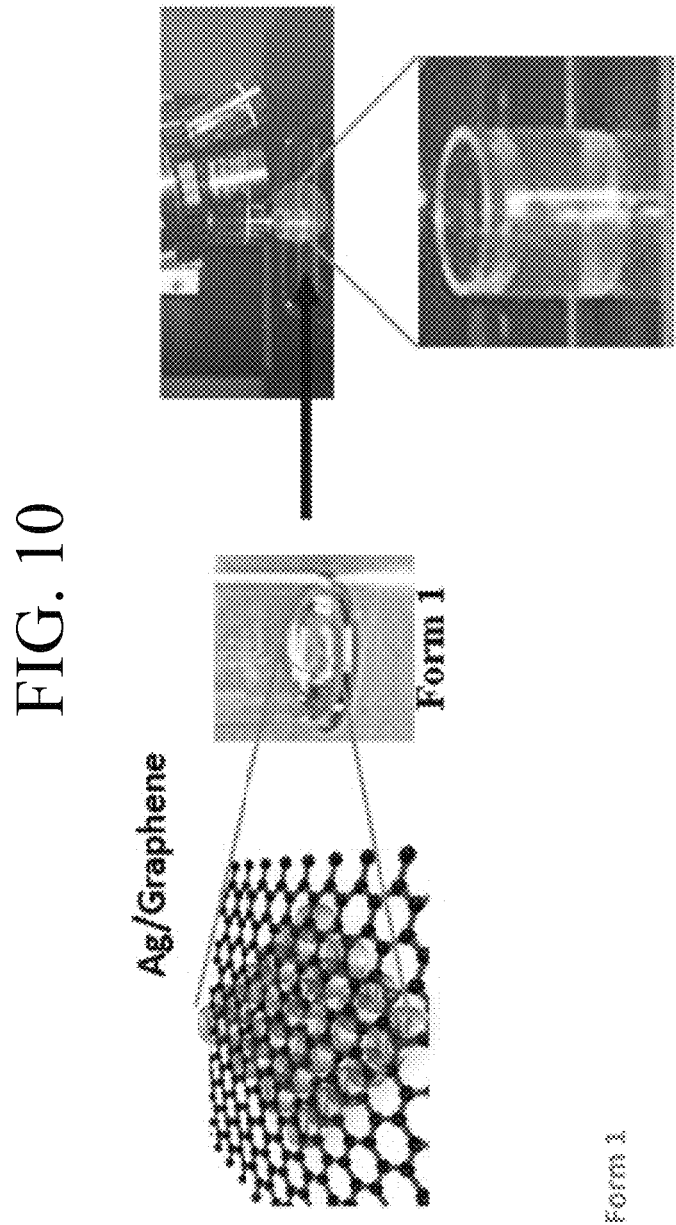
FIG. 10. Form 1 sample holder design for Raman measurements.
Figure 11:
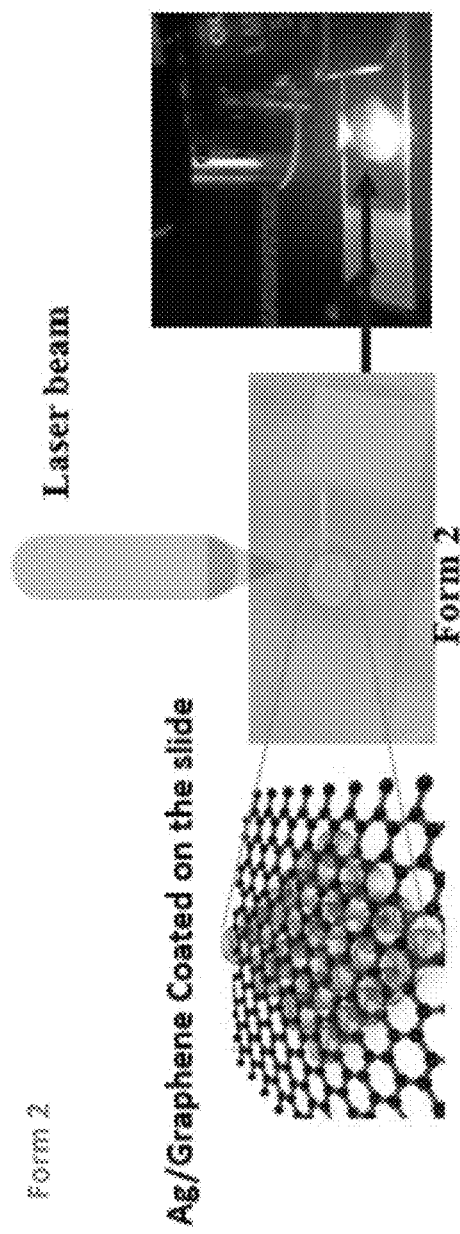
FIG. 11. Form 2 sample holder design for Raman measurements.

Sample Holder Design. The sample holders were designed in two shapes or forms. First design was a holder in for of cuvette with dimensions of 0.5 to 2 cm in diameter and 0.3 to 2 cm in length, as shown in Scheme 1 (FIG. 10). The second form is the design of slides where the prepared nanomaterials were coated on the surface of the silica glass slides with dimensions of 3 to 10 cm in length and 1 to 5 cm in width, Scheme 2 (FIG. 11). The thickness of the layer of the coated materials was in the nano to micro meter size.

Surface-Enhanced Raman Scattering ("SERS") spectroscopy. The SERS spectra of samples were obtained by using a Raman spectroscopy system—a Lab Ram HR Evolution Raman spectrometer—equipped with an internal He—Ne 17 mW laser at a 633 nm excitation wavelength. SERS samples were prepared in a small cuvette by using a 4:1 volume ratio of aqueous MTZ solution to G-D-Ag. A 50× objective was used for focusing the laser beam to the solution. The data acquisition time was 20 sec with one accumulation for collection with each SERS spectra. A cuvette with dimensions of 1 cm radius and 2 cm height was used as a sample cell for the Raman spectra. The SERS spectra were obtained in the range from 400-2000 cm$^{-1}$.

Figure 3:
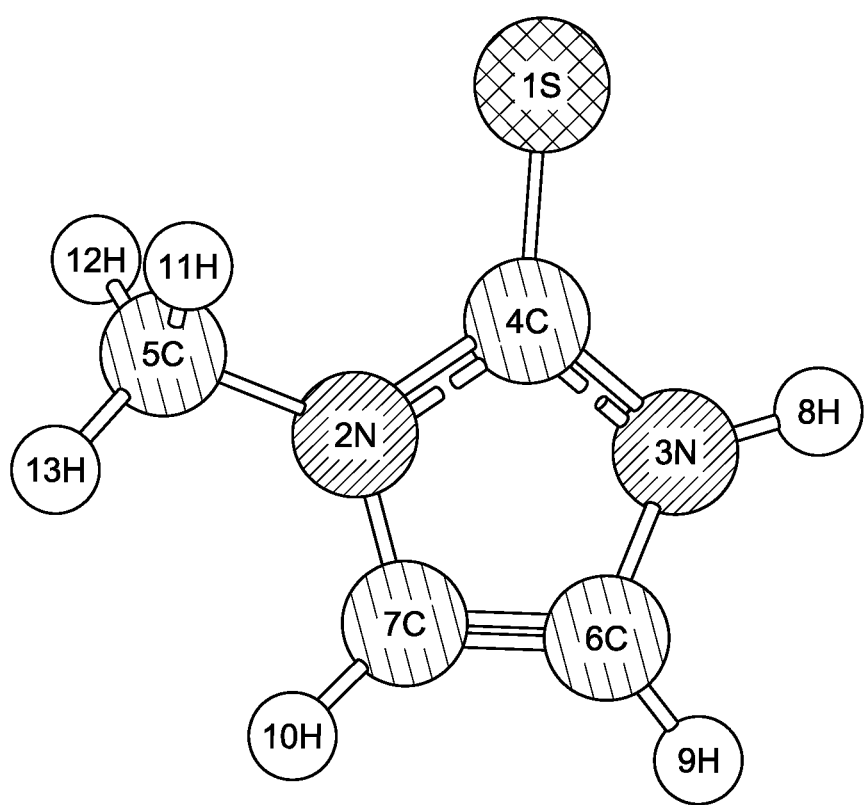
FIG. 3. The optimized structure of MTZ.

Theoretical Calculations. Density functional theory (DFT) calculations were employed to optimize the structure of MTZ and calculate its vibrational frequencies at the ground level. The Gaussian 09 program was used to carry out the DFT-B3LYP/6-311++G(d,p) level of calculation. See Gaussian 09, Revision D.01, Frisch M. J., et al., Gaussian, Inc., Wallingford Conn., (2013), incorporated herein by reference in its entirety. Atomic displacements associated with each vibrational mode were carefully inspected using Gauss-View software and corresponding potential energy distributions (PEDs) were computed with Vida software in order to provide reliable assignments of the normal Raman, as well as SERS spectra, of MTZ. See GaussView, Version 5.0, R. Dennington II, T. Keith, J. Millam, Semichem Inc., Shawnee Mission, K S, 2009; and Jamróz M. H. Vibrational Energy Distribution Analysis: VEDA 4, program, Warsaw, 2004-2010, each incorporated herein by reference in its entirety. The minimum-energy structure of MTZ with atom numbering adopted is shown in FIG. 3. The vibrational frequencies were compared to the solid state Raman spectra (Table 1).

Figure 4:
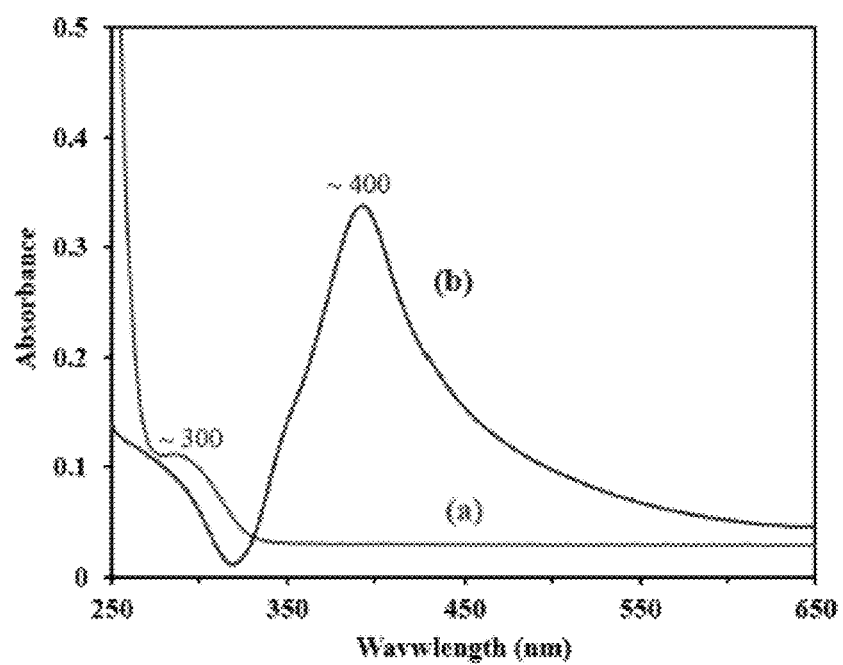
FIG. 4. UV-Vis absorption spectra of (a) the G-D and (b) the G-D-Ag.

Structural Analysis of G-D and G-D-Ag. The ultraviolet-visible spectra of G-D and G-D-Ag are shown in FIG. 4. The maximum absorption band at 300 nm is attributed to the n–π* electronic transitions of the dendrimer. Moreover, the maximum absorption peak of G-D-Ag is at 400 nm, due to the plasmon resonance of G-D-Ag, indicating the formation AgNPs on the surface of the dendrimer.

Figure 5:
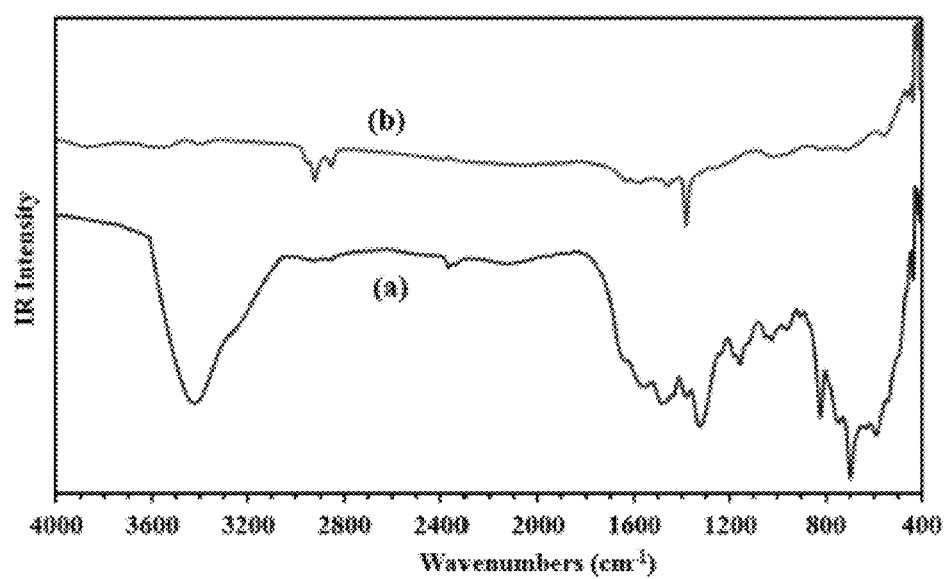
FIG. 5. FT-IR spectra of (a) G-D and (b) G-D-Ag.

FT-IR was employed to confirm the chemical structure of G-D and G-D-Ag. FIG. 5 shows the FT-IR spectra of G-D and G-D-Ag. The FT-IR spectrum of G-D shows a weak broadband at 3418 $cm^{-1}$, corresponding to the vibration of $NH_2$. The very low-intensity peaks at 2923 $cm^{-1}$ and at 2854 $cm^{-1}$ are assigned to the symmetric and antisymmetric stretching vibrations of CH2, respectively. The bands at 1654 and 1324 $cm^{-1}$ are assigned to C=C and C=O, respectively. The FT-IR spectrum of G-D-Ag differs from that of G-D, as evidenced by the weakening of the $NH_2$ band in the range 3350 to 3450 $cm^{-1}$. It suggests that the AgNPs are stabilized in the G-D network through this functional group. See Shen, J. et al. *One Step Synthesis of Graphene Oxide-Magnetic Nanoparticle Composite*. J. Phys. Chem. C, 114, 1498-1503 (2010), incorporated herein by reference in its entirety. The disappearance of the peak, attributed to C—O at 1324 $cm^{-1}$ in the G-D-Ag spectrum, is probably due to the reduction of the oxygenated functional groups through the heat treatment process. See Rajesh et al.

Figure 6E:
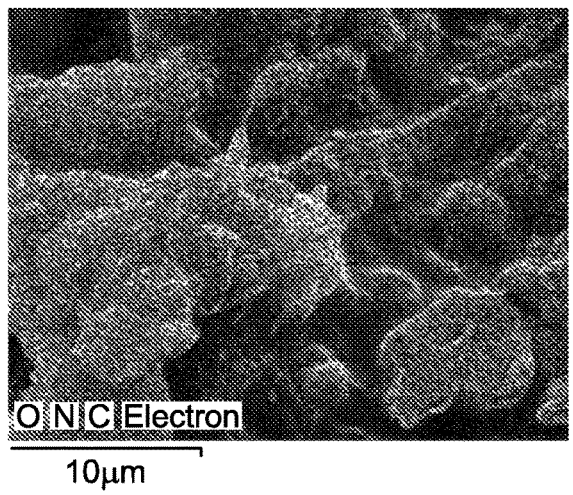
FIG. 6E. Mapping image of G-D.
Figure 6F:
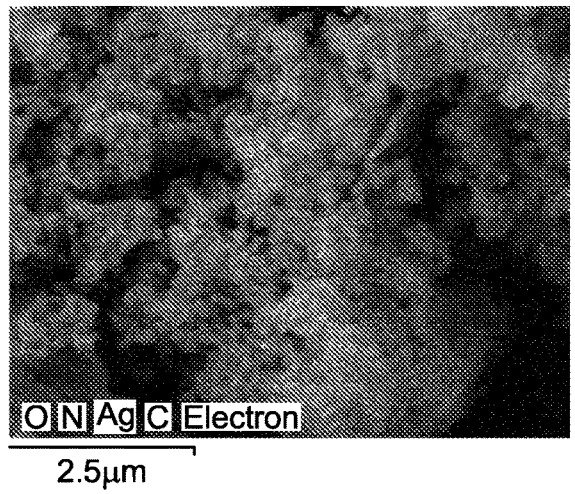
FIG. 6F. Mapping image of G-D-Ag.
Figure 6G:
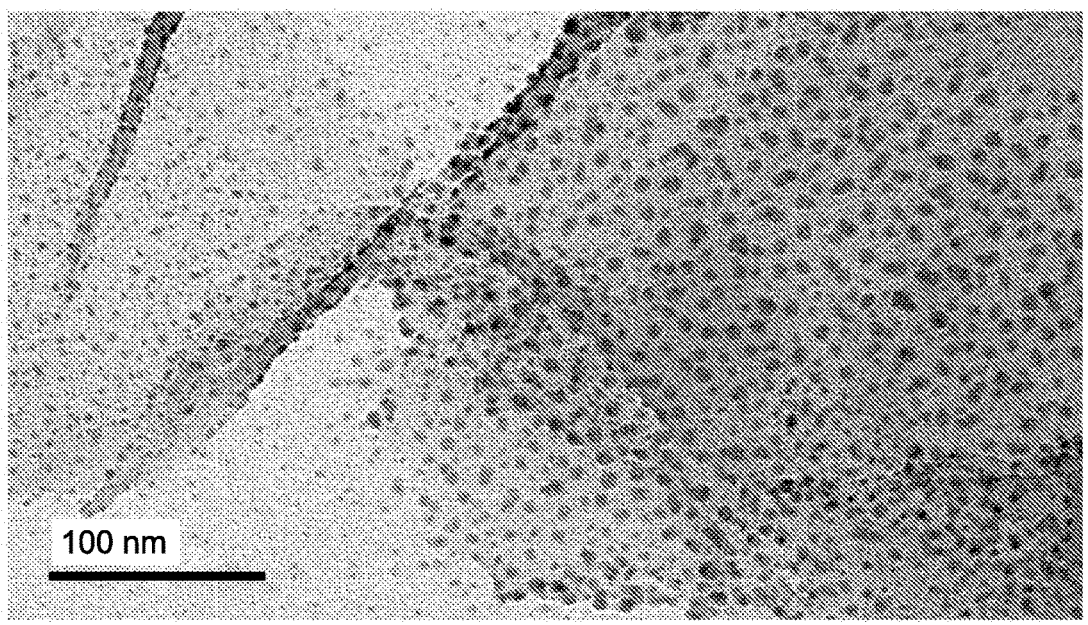
FIG. 6G. TEM image of G-D-Ag.

SEM, EDX and mapping imagings were used as techniques complementary to TEM to investigate the appearance of the synthesized materials, as seen in FIG. 6. The SEM images (FIG. 6A), shows the morphology of the prepared G-D, and the inset TEM image illustrates the formation of multi-dots of dendrimers on the graphene nanosheets. These dots are used as bases, or cores, for attracting and catching the silver ions. The presence of reactive amine groups on the surface of dendrimer-modified graphene was profited to allow e multipoint attachment of the AgNPs through the formation of linkages, (as shown in the mechanism FIG. 2) which were further transformed to stable secondary amino linkages by reductive treatment with $NaBH_4$. This allows for the controlled growth of AgNPs, as shown in the TEM image (FIG. 6G) and the SEM image, with TEM inset (FIG. 6B), which provide evidence that the Ag nanoparticles are well dispersed as a consequence of the stabilization of the growing silver by the different amide groups of the dendrimer. The nanoparticles could be stabilized by interaction with the primary amino groups remaining at the outer surface of the dendrimer. The mapping images, FIGS. 6E and 6F, indicate that the stabilized AgNPs were mostly uniform dispersed. Further characterization was confirmed by EDX spectra (FIGS. 6C and 6D), which confirms the presence of the silver, with strong interaction with the dendrimer, even after washing the sample several times, followed by drying. Therefore, the graphene was successfully used as an indirect support or the silver nanoparticles. The silver nanoparticles were decorated on the dendrimer branches rather than being directly attached to the graphene. This material provides the best SERS enhancement for MTZ compared with the AgNPs loaded graphene, because the dendrimer allows better distribution of AgNPs on the nanosheets, as shown in the TEM image. Therefore, the role of the graphene was as a support; however, the silver nanoparticles were located on the dendrimer branches (linkers) rather directly attached on the graphene. This way the silver nanoparticles were better distributed and decorated on the graphene sheets surface as shown in the TEM image.

Figure 7:
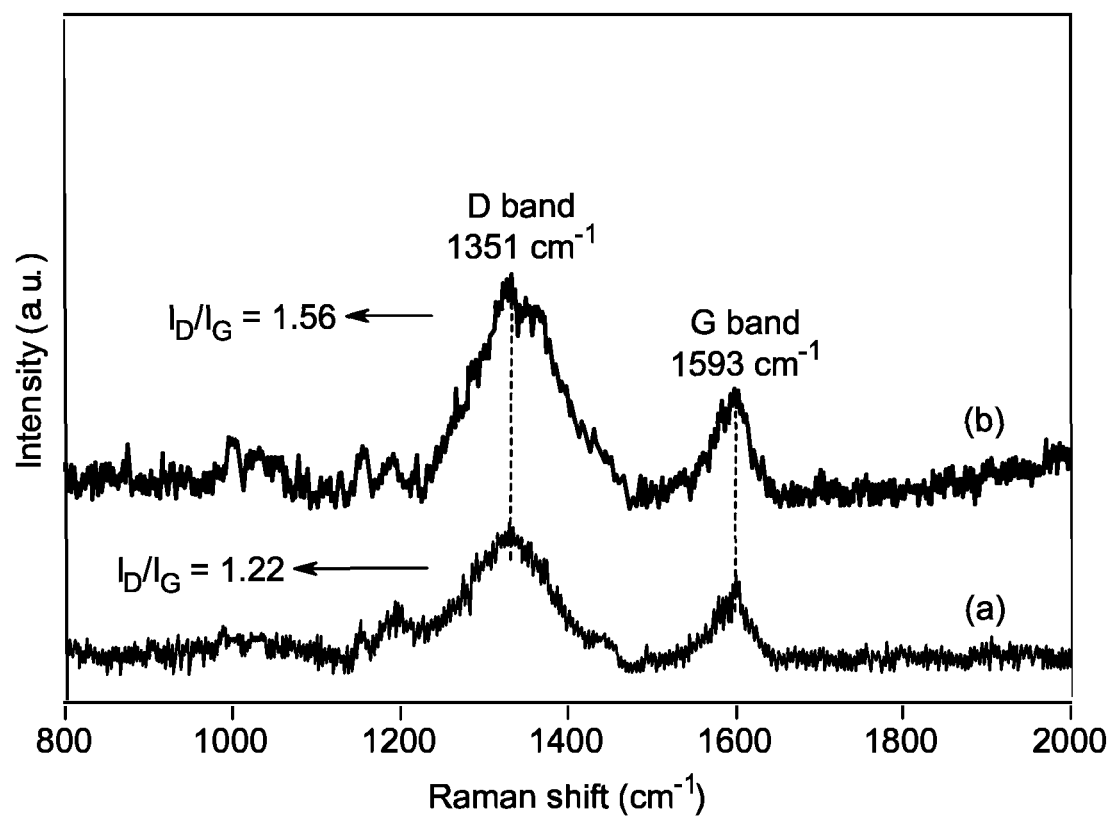
FIG. 7. Raman spectra of (a) G-D and (b) G-D-Ag.

Raman Analysis of G-D and G-D-Ag. The Raman spectra of the G-D and G-D-Ag are shown in FIG. 7. The Raman spectra of all samples displayed two prominent bands. While the D band around 1350 $cm^{-1}$ is associated with disordered sp3 carbon atoms, the G band around 1590 $cm^{-1}$ corresponds to ordered sp2-hybridized carbon atoms. See Sarkar, S., Bekyarova, E., Niyogi, S., Haddon, R. C. Diels-Alder Chemistry of Graphite and Graphene: *Graphene as Diene and Dienophile*. J. Am. Chem. Soc. 133, 3324-3327 (2011), incorporated herein by reference in its entirety. Further, the intensity ratio of D and G bands (ID/IG) increases. The ID/IG is used to assess the sp2/sp3 carbon ratio, which represents the degree of disorder and the average size of the sp2 carbon atoms domains. The ratio for G-D-Ag, 1.56, was larger than that for G-D, 1.22, suggesting that more graphitic domains are formed and the sp2 cluster number is increased after introducing the silver via the reduction process. This reflects the functionalization of the AgNPs on the dendrimer-modified graphene. See Fang M., Wang K., Lu H., Yang Y. & Nutt S. Covalent polymer functionalization of graphene nanosheets and mechanical properties of composites. J. Mater. Chem. 19, 7098-.7105 (2009), incorporated herein by reference in its entirety. This can be explained by the removal of some oxygen-containing functional groups during the reduction process, leading to the formation of high-level fragmentation along the reactive sites of graphene dendrimer. See Lin-jun, H. et al. *Preparation of Graphene/Silver Nanohybrid Composite with Good Surface-Enhanced Raman Scattering Characteristics*. Int. J. Electrochem. Sci., 11 398-405 (2016), incorporated herein by reference in its entirety.

Figure 8:
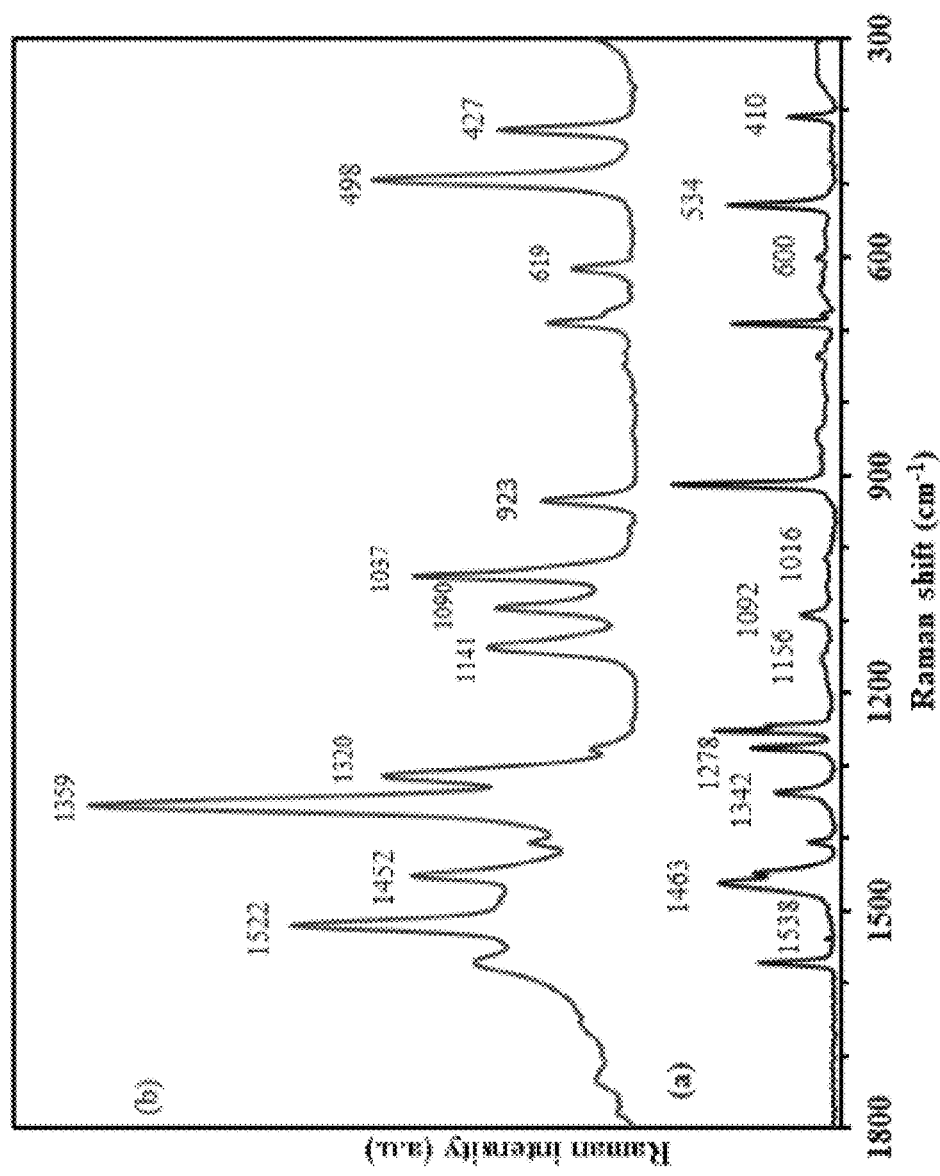
FIG. 8. Raman spectrum of (a) pure solid MTZ and (b) SERS spectrum of $1\times10^{-5}$ M MTZ with G-D-Ag as a substrate, Laser $\lambda$=633 nm, acquisition time; 20 sec, and objective; 50×.

Surface-Enhanced Raman Scattering (SERS) spectra of MTZ with G-D-Ag. The collected Raman spectrum for solid MTZ, compared with a $1 \times 10^{-5}$ M concentration MTZ-(G-D-Ag) SERS spectrum, is depicted in FIG. 8. In order to understand the nature of the interaction between the bounding of the MTZ molecules and the surface of the AgNPs, it is useful to propose proper band assignments for the normal Raman and SERS spectra. For reliable assignments, we conducted DFT assessments of the vibrational frequencies of the single MTZ molecule and compared them with the corresponding ones resulting from the interaction between the silver and MTZ. All these data are listed in Table 1.

The DFT method based on the hybrid B3LYP functional and split-valence 6-311++G(d,p) basis set showed good agreement with the experimental results. The band observed at 1342 $cm^{-1}$ and at 1345 $cm^{-1}$ in the solid and solution Raman spectra, respectively, shifted to 1359 cm-1 in the SERS spectrum. This band shows the highest enhancement factor. The DFT calculation attributes this band mostly to the N2-C4 stretching (with some contribution from the ring and C6-N3-H bending) and successfully predicts its slight shift to the lower frequency side. Moreover, the modes observed at 1538 and 1463 cm$^{-1}$ have shifted to 1522 and 1452 cm$^{-1}$, respectively, in the SERS spectrum with significant enhancement. PED analysis shows that these bands are associated with S—C and C—N stretching modes (Table 1). The bands at 1278, 1156, 1092, 1016, and 600 cm$^{-1}$ in the normal Raman spectrum are shifted to 1320, 1141, 1090, 1037, and 619 cm$^{-1}$, respectively in the SERS spectrum. These bands show higher intensities in the SERS spectrum.

311++G(d,p) basis set showed good agreement with the experimental results. The band observed at 1342 cm$^{-1}$ and at 1345 cm$^{-1}$ in the solid and solution Raman spectra, respectively, shifted to 1359 cm-1 in the SERS spectrum. This band shows the highest enhancement factor. The DFT calculation attributes this band mostly to the N2-C4 stretching (with some contribution from the ring and C6-N3-H bending) and successfully predicts its slight shift to the lower frequency side. Moreover, the modes observed at 1538 and 1463 cm$^{-1}$ have shifted to 1522 and 1452 cm$^{-1}$, respectively, in the SERS spectrum with significant enhancement. PED analysis shows that these bands are associated with S—C and C—N stretching modes (Table 1). The bands at 1278, 1156, 1092, 1016, and 600 cm$^{-1}$ in the normal Raman spectrum are shifted to 1320, 1141, 1090, 1037, and 619 cm$^{-1}$, respectively in the SERS spectrum. These bands show higher intensities in the SERS spectrum.

TABLE 1

Infrared, Raman, SERS and calculated DFT vibrational frequencies (cm$^{-1}$) of MTZ.

| Obs. | | | | Calc. | | Assignments with |
| --- | --- | --- | --- | --- | --- | --- |
| IR | Raman (Solid) | Raman (Solution) | SERS | MTZ | MTZ-Ag | Corresponding PEDs (%) |
| | | | | 3531 | 3366 | 100% ν (N3—H) |
| 3159 w | 3161 w | 3166 m | | 3162 | 3166 | 97% ν (C7—H) |
| 3104 w | 3105 w | 3106 vw | | 3142 | 3147 | 98% ν (C6—H) |
| 3012 w | | | | 3022 | 3021 | 95% ν (C5—H11) |
| | | | | 2999 | 2995 | 100% ν (C5—H12) |
| 2949 vw | 2950 m | 2960 m | 2945 m | 2936 | 2932 | 96% ν (C5—H13) |
| 1578 vs | 1579 s | 1580 m | 1567 w | 1588 | 1581 | 63% ν (C6=C7), 10% δ (N3—H) bend |
| | 1538 vw | | 1522 vs | 1509 | 1496 | 24% ν (N2—C4), 15% ν (C—C), 38% δ (H11—C—H12) bend |
| | | | | 1473 | 1467 | 23% ν (S—C4), 14% ν (C4—N) bend, 10% δ (N3—H) bend, |
| | 1479 vw | 1480 vs | | 1466 | 1457 | 72% δ CHMe scissoring |
| 1462 s | 1463 vs | 1460 vw | 1452 s | 1459 | 1452 | 23% ν (S—C4), 14% ν (N3—C4), 12% δ (C—H)bend, |
| 1403 m | 1410 m | 1410 vw | 1408 w | 1415 | 1411 | 14% ν (N2—C4), 14% ν (N3—C6), 13% ν (S—C4), 30% δ (C—H)bend |
| 1339 vs | 1342 s | 1345 s | 1359 vs | 1315 | 1328 | 32% ν (N2—C4), 11% δ ring bend, 19% δ C6—N3—H bend |
| 1274 s | 1278 m | 1281 m | 1320 s | 1285 | 1309 | 15% ν (N2—C5), 19% δ N3—H(C6—H)bend, 14% δ ring breathing |
| 1248 m | 1252 vs | 1255 vw | 1277 vw | 1212 | 1237 | 51% ν (N3—C4), 18% δ N3—H(C6—H)bend, 13% δ (C7—H)bend |
| 1152 vs | 1156 vs | 1153 m | 1141 m | 1159 | 1150 | 16% ν (N3—C6), 16% ν (S—C4), 15% δ (H11—C—H12) rock, |
| 1086 vw | 1092 m | 1088 vw | 1090 m | 1089 | 1091 | 46% ν (N3—C6), 14% δ (N3—H) bend, 21% δ (C7—H)bend |
| 1014 s | 1016 m | 1017 vw | 1037 m | 1013 | 1022 | 15% ring CH bend, 13% δ CH$_{Me}$ bend, 41% δ ring bend, |
| 913 m | 915 vs | 916 s | 937 w | 913 | 923 | 12% ν (N2—C4), 12% δ N3—H(C6—H) bend, 62% δ ring bend |
| 818 w | 810 vw | | 830 vw | 806 | 818 | 89% γ (H—C6—C7—H) twist |
| 673 vs | 679 vw | 684 vs | 687 w | 685 | 699 | 25% δ (C7—N2—C5) bend, 15% δ (C4—N2—C5) bend |
| | | 643 vw | | 670 vw | 650 | 667 | 47% ring CH bend, 39% γ (N3—C4—N2) |
| 599 vw | 600 vw | 602 vw | 619 m | 603 | 623 | 78% γ CN ring bend. |
| 527 vs | 525 m | 522 w | 498 s | 534 | 520 | 53% δ (S—C4—N3) bend, 25% δ (S—C4—N2), |
| | 493 vw | | | 503 | 569 | 84% γ (N3—C6—C7) |
| 411 s | 410 s | 410 m | 427 m | 411 | 421 | 71 % δ (S—C4—N2) |
| | 264 m | 260 m | 279 w | 238 | 251 | 85% γ (C4—S) wag |
| | 208 vw | 209 vw | | 207 | 220 | 76% γ ring |

SERS Enhancement Factors of MTZ. The SERS enhancement factors (EFs) for the vibrations of MTZ ($1\times10^{-3}$ M) on G-D-Ag to the corresponding band obtained from 1.0 M saturated solution were calculated using the following equation:

$$EFs = (\delta \text{ SERS} \times C \text{ normal})/(\delta \text{ normal} \times C \text{ SERS});$$

where $\delta$ and $C$ are the Raman mode intensity and sample concentrations, respectively. The EFs for the SERS peaks of MTZ on G-D-Ag are given in Table 2. The EFs are not the same for the different MTZ modes; the maximum enhancement was observed at 1342 cm$^{-1}$.

TABLE 2

SERS enhancement factor of MTZ on G-D-Ag substrate.

| SERS spectra (cm$^{-1}$) | Enhancement Factor (EF) |
|---|---|
| 1522 | $8.3 \times 10^4$ |
| 1452 | $1.1 \times 10^4$ |
| 1359 | $1.5 \times 10^4$ |
| 1320 | $2.5 \times 10^4$ |
| 1141 | $1.0 \times 10^4$ |
| 1090 | $2.3 \times 10^4$ |
| 1037 | $3.8 \times 10^4$ |
| 619 | $1.4 \times 10^4$ |
| 498 | $2.0 \times 10^4$ |
| 427 | $2.4 \times 10^4$ |

Figure 9A:
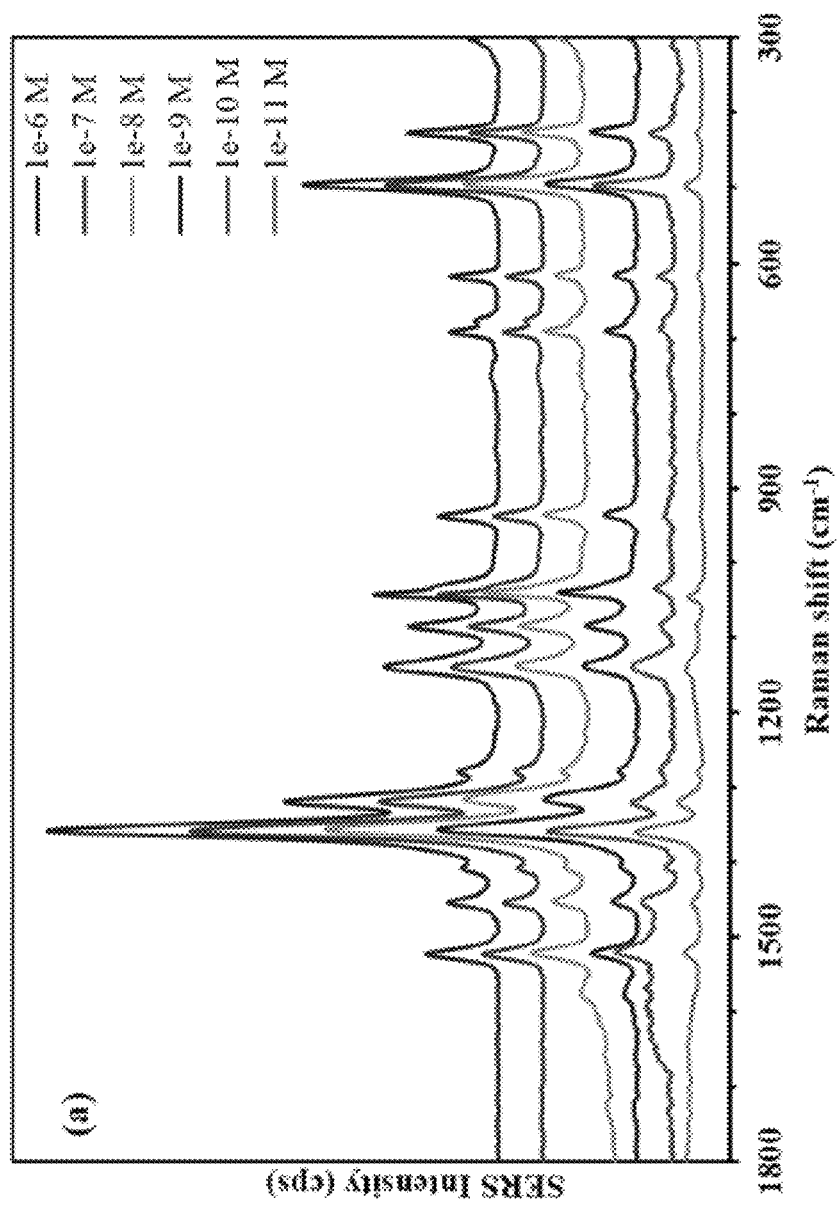
FIG. 9A. SERS spectra of MTZ with different concentration using G-D-Ag. Spectral plots appear in the order indicated with 1e-6 M being the uppermost plot and 1e-11 M being the lowermost.
Figure 9B:
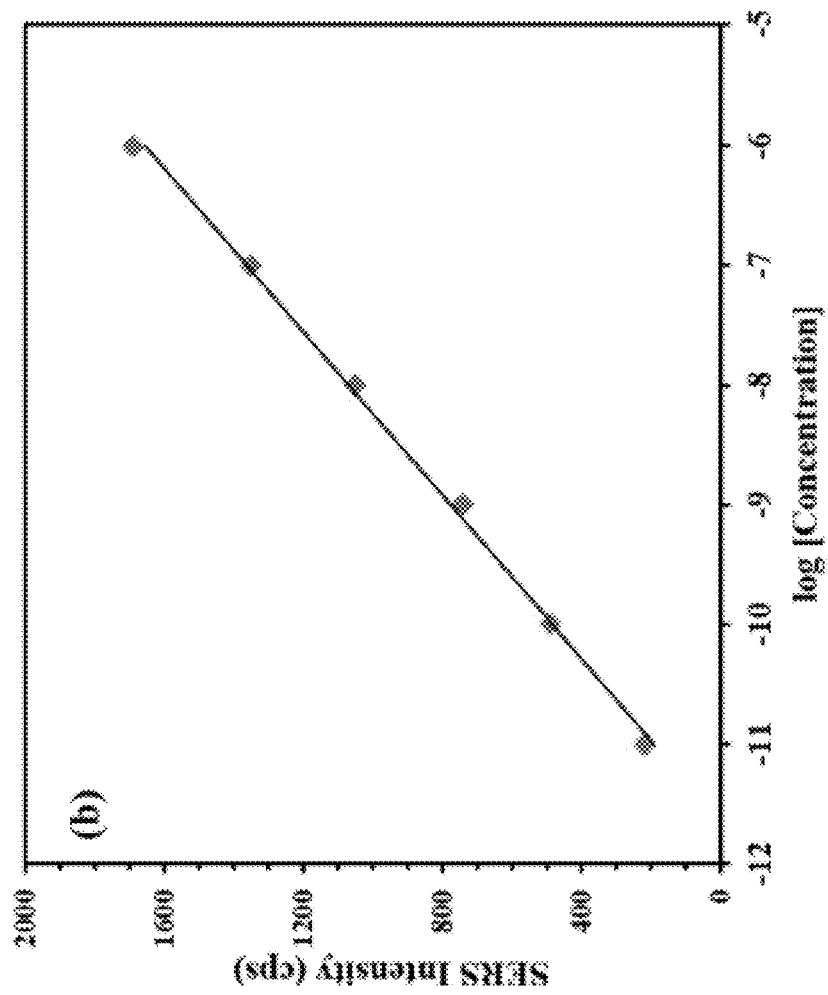
FIG. 9B. Calibration curve of the band at 1359 $cm^{-1}$. Laser $\lambda$=633 nm, acquisition time; 20 sec, and objective; 50×.

SERS Spectra of MTZ at Different Concentrations. The SERS spectra of MTZ aqueous solution with G-D-Ag as a substrate at different concentrations are given in FIG. 9A. The intensities of the SERS spectra increase with an increase in the concentration of MTZ. This suggests that the SERS intensities are proportional to the molecular quantity of MTZ. The highest enhanced band, at 1359 cm$^{-1}$ in the SERS spectra, was selected for creating a qualitative analysis of MTZ. A plot of the ERS response versus the logarithmical scale of $10^{-6}$ M to $10^{-11}$ M of MTZ at 1359 cm$^{-1}$ was obtained, (FIG. 9B), showing a good coefficient of determination (R$^2$) of 0.9976. Within the dynamic range, the lowest concentration measured in the SERS analysis of the MTZ solution was $10^{-11}$ M. To evaluate the analytical performance of the proposed method, parameters such as linearity, repeatability, limits of detection and dynamic range were investigated under optimum experimental conditions. The results of the linear equations, dynamic range, and R2 for the obtained calibration curves of MTZ with G-D-Ag substrate are summarized in Table 3.

TABLE 3

Regression equation between Raman intensities and concentrations of MTZ and their coefficient of determination (R$^2$).

| Raman Peaks | Regression Equation | R$^2$ | Dynamic linear range (M) | LOD* (M) |
|---|---|---|---|---|
| 1359 cm$^{-1}$ | y = 292.43x + 3409.8 | 0.9976 | $10^{-6} - 10^{-11}$ | $1.43 \times 10^{-12}$ |
| 1320 cm$^{-1}$ | y = 144.97x + 1651.9 | 0.9921 | $10^{-6} - 10^{-11}$ | $2.67 \times 10^{-12}$ |
| 498 cm$^{-1}$ | y = 124.14x + 1479 | 0.9744 | $10^{-6} - 10^{-11}$ | $3.71 \times 10^{-12}$ |
| 427 cm$^{-1}$ | y = 63.771x + 739.39 | 0.9651 | $10^{-6} - 10^{-11}$ | $0.91 \times 10^{-11}$ |

Good linear relations between the enhanced SERS bands' intensities and the logarithmical scale of MTZ concentrations were noted with a wide dynamic linear range or linear working range (LWR) for MTZ with the substrate. The precision of the proposed method was checked by replicate analysis of the working standard of MTZ drug at six concentration levels. The relative standard deviation (RSD) for all concentration levels was <2.2%, which indicates both the precision and repeatability of the proposed method. The reproducibility of the method using the same batch of the prepared material was obtained in five days, with a corresponding relative average standard deviation of less than 4%.

The results obtained by the reported method in this study were compared with some methods reported in the literature in terms of calibration range, detection limits, and determination coefficients (R$^2$). The comparison with other methods for the determination of MTZ is summarized in Table 4. In comparison to other methods for determination of the MTZ, the proposed method has attracted more interest due to its sensitivity, good dynamic range, and simplicity.

TABLE 4

Comparison of Dynamic linear range, detection limits between and coefficient of determination (R$^2$) this method and other methods for the determination of MTZ.

| Method | Dynamic linear range (M) | Limit of detection (M) | R$^2$ | Ref. |
|---|---|---|---|---|
| SERS | $10^{-6}$-$10^{11}$ | See Table 3 | See Table 3 | Present work |
| SERS | $5.0 \times 10^{-8}$-$5.5 \times 10^{-7}$ | $7.4 \times 10-05$ | 0.998 | 29 |
| SERS | $1.8 \times 10^{-9}$-$1.3 \times 10^{-6}$ | $8.8 \times 10^{-10}$ | 0.9992 | 30 |
| Flow-Injection | $1.75 \times 10^{-5}$-$8.75 \times 10^{-4}$ | $8.75 \times 10^{-6}$ | 0.999 | 31 |
| Capillary Electrophoresis | $1.0 \times 10^{-7}$-$2.0 \times 10-4$ | $5.0 \times 10^{-8}$ | 0.9995 | 32 |
| DPV | $1.0 \times 10^{-7}$-$2.0 \times 10^{-5}$ | $2.0 \times 10^{-8}$ | 0.998 | 33 |
| HPLC | $0.2 \times 10^{-6}$-$2.0 \times 10^{-6}$ | $0.18 \times 10-06$ | 0.9975 | 34 |
| SWV | $6.0 \times 10^{-6}$-$240 \times 10^{-6}$ | $1.98 \times 10^{-6}$ | 0.9996 | 35 |

Application of the proposed method for the determination of MTZ in real samples. Determination of MTZ in tablet samples was examined to demonstrate the ability of the SERS method for the determination of MTZ in real samples. The proposed method was applied for the determination of MTZ in the commercial pharmaceutical dosage forms, tablet samples. In order to access the matrix effect, the relative recoveries of the method were calculated. The obtained results, shown in Table 5, indicate the accuracy of the method, as well as the low interference limits caused by the frequently encountered excipients and the degradation products. Thus, the SERS method retained its efficiency for the determination of MTZ in real samples.

TABLE 5

Determination of MTZ in pharmaceutical tablet samples (n = 3); Recovered concentrations obtained for MTZ using a SERS method with G-D-Ag and calibration curve at 1369 cm$^{-1}$ (n = 3).

| Sample | Expected | Found | Recovery % | Confidence interval | Bias (%) |
| --- | --- | --- | --- | --- | --- |
| Tablet 1 | 5 mg/g | 4.93 mg/g | 98.6 | $0.31 \times 10^{-6}$ M | −1.4 |
| Tablet 2 | 5 mg/g | 4.88 mg/g | 97.6 | $0.31 \times 10^{-6}$ M | −2.4 |
| Spiked 1 | $2.5 \times 10^{-6}$ M | $2.61 \times 10^{-6}$ M | 104.4 | $0.48 \times 10^{-6}$ M | +4.4 |
| Spiked 3 | $5.0 \times 10^{-6}$ M | $5.13 \times 10^{-6}$ M | 102.6 | $0.72 \times 10^{-6}$ M | +2.6 |

As shown herein, the inventors have synthesized graphene functionalized with polyamidoamine dendrimer decorated with silver nanoparticles (G-D-Ag) and characterized it by using various techniques including SEM, TEM, FTIR and UV.

The SERS method was exploited to record the vibrational frequencies of MTZ adsorbed on G-D-Ag. The optimized conformation and vibrational assignments of MTZ were carried out using a DFT calculation with a B3LYP/6-311++G (d,p) basis set. The vibration assignments and the wave number of vibration frequency bands in the theoretical spectra were in agreement with those of the experimental spectra. Most of the bands related to N and S atom were apparently enhanced and slightly shifted. These results confirm that MTZ molecules were adsorbed on the G-D-Ag, probably through the lone pair on the N and S atoms. The correlation between the logarithmical scale of MTZ concentration and the SERS signal was linear within a dynamic range of $10^{-6} \pm 10^{-11}$ and $R^2$ of 0.9976, and with good detection limits down to $1.43 \times 10^{-12}$ (or any intermediate value or subrange). This detection limit was calculated as three-times the baseline noise. The experimental detection limit was $1 \times 10^{-11}$ M.

Terminology. Terminology used herein is for the purpose of describing particular embodiments only and is not intended to be limiting of the invention.

The headings (as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent Applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for detecting methimazole ("MTZ") in a sample, comprising:
   contacting the sample containing MTZ with a substrate comprising graphene-dendrimer-stabilized silver nanoparticles (G-D-Ag) to adsorb the MTZ onto the G-D-Ag, and
   performing surface-enhanced Raman scattering (SERS) by exposing the substrate with the G-D-Ag adsorbed MTZ to a focused laser beam and recording one or more vibrational frequencies,
   determining the presence of MTZ by the one or more vibrational frequencies emitted by the SERS;
   wherein the G-D-Ag comprise:
      a graphene oxide sheet chemically bonded with at least 2 polyamidoamine ("PAMAM") dendrimers through carboxamide bonds as represented by formula (I):

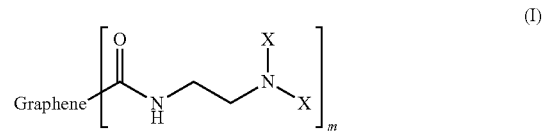

wherein X is -A-B—$NH_2$, -A-B—N-(A-B—$NH_2$)$_2$, or -A-B—N-[A-B—N-(A-B—$NH_2$)$_2$]$_2$;
   A is —$CH_2CH_2C(O)$—;
   B is —$NHCH_2CH_2$—;
   Graphene represents the graphene oxide sheet; and
   m is a positive integer in the range of 2-100;
   and silver nanoparticles bound to the graphene oxide sheet supported polyamidoamine ("PAMAM") dendrimer;
   wherein a weight ratio of the silver nanoparticles relative to the graphene oxide sheet is in the range of 1:1 to 3:1.

2. The method of claim 1, wherein the silver nanoparticles of the G-D-Ag have a mean diameter of no more than 37 nm.

3. The method of claim 1, wherein the silver nanoparticles of the G-D-Ag have a mean diameter of no more than 18 nm.

4. The method of claim 1, wherein the substrate comprises silica glass coated with at least one layer of the G-D-Ag.

5. The method of claim 1, wherein the substrate comprises silica glass coated with at least one layer of the G-D-Ag, wherein said at least one layer of G-D-Ag in aggregate ranges in thickness from 10 nm to 100 μm.

6. The method of claim 1, further comprising:

mixing the at least one sample with the G-D-Ag at a volume ratio of 1:1 to 8:1 to prepare at least one analyte containing the G-D-Ag adsorbed MTZ; and determining the presence of the MTZ in the at least one sample by comparing the peak intensity of a Raman band of methimazole obtained from the SERS spectrum of the at least one analyte to a standard linear regression curve that plots known concentrations of methimazole against peak intensities of the Raman band.

7. The method of claim 1, wherein the sample is a pharmaceutical, drug or chemical sample and not a biological sample from a subject.

8. The method of claim 1, wherein the sample is obtained from *Felis catus* (domestic cat) or other member of the family Felidae.

9. The method of claim 1, wherein the sample is from a subject having hyperthyroidism or at risk thereof.

10. The method of claim 1, wherein the sample is from a female who is pregnant or who may become pregnant.

11. The method of claim 1, wherein the sample is from a subject having, genetically predisposed to having, or at risk of having agranulocytosis, aplastic anemia (pancytopenia), ANCA-positive vasculitis, exfoliative dermatitis, hepatitis, or hepatic dysfunction or at least one symptom thereof; or wherein the sample is from a subject having anorexia, pruritus, or right upper quadrant pain or other symptom of hepatic dysfunction or wherein the sample is from a subject having an abnormal liver function test.

* * * * *